US009702808B2

(12) United States Patent
Lin

(10) Patent No.: US 9,702,808 B2
(45) Date of Patent: Jul. 11, 2017

(54) METHOD AND APPARATUS FOR BULK MICROPARTICLE SORTING USING A MICROFLUIDIC CHANNEL

(71) Applicant: Namocell Inc., Palo Alto, CA (US)

(72) Inventor: Junyu Lin, Palo Alto, CA (US)

(73) Assignee: Namocell Inc., Palo Alto, CA (US)

( * ) Notice: Subject to any disclaimer, the term of this patent is extended or adjusted under 35 U.S.C. 154(b) by 0 days.

(21) Appl. No.: 15/377,869

(22) Filed: Dec. 13, 2016

(65) Prior Publication Data

US 2017/0089826 A1    Mar. 30, 2017

Related U.S. Application Data

(63) Continuation-in-part of application No. PCT/US2014/047152, filed on Jul. 18, 2014, which is a continuation of application No. 14/216,185, filed on Mar. 17, 2014, now Pat. No. 8,820,538.

(60) Provisional application No. 62/323,162, filed on Apr. 15, 2016.

(51) Int. Cl.
| | | |
|---|---|---|
| G01N 15/00 | (2006.01) | |
| G01N 15/14 | (2006.01) | |
| B01L 3/00 | (2006.01) | |
| G01N 15/10 | (2006.01) | |

(52) U.S. Cl.
CPC .... *G01N 15/1484* (2013.01); *B01L 3/502715* (2013.01); *B01L 3/502753* (2013.01); *B01L 3/502761* (2013.01); *B01L 2200/0605* (2013.01); *B01L 2200/0652* (2013.01); *G01N 2015/0065* (2013.01); *G01N 2015/1006* (2013.01); *G01N 2015/149* (2013.01)

(58) Field of Classification Search
CPC ........ B01L 3/502784; B01L 3/502769; B01L 2200/0647; B01L 2200/0652; B01L 2300/0861; B01L 2300/0864; B01L 2300/0867; G01N 15/1484; G01N 15/1459; G01N 2015/1081; G01N 2015/149; B07C 5/3425
See application file for complete search history.

(56) References Cited

U.S. PATENT DOCUMENTS

| | | | | |
|---|---|---|---|---|
| 3,710,933 A | | 1/1973 | Fulwyler et al. | |
| 4,175,662 A | | 11/1979 | Zold | |
| 4,756,427 A | * | 7/1988 | Gohde | ............... G01N 15/1404 209/3.1 |
| 4,936,465 A | * | 6/1990 | Zold | ......................... B07C 3/02 209/3.1 |

(Continued)

OTHER PUBLICATIONS

Perkin Elmer; FlexDrop PLUS Precision Reagent Dispenser (product information); 4 pgs.; © 2007 (year of pub. sufficiently earlier than effective US filing date and any foreign priority date).

(Continued)

*Primary Examiner* — Joseph C Rodriguez
(74) *Attorney, Agent, or Firm* — Shay Glenn LLP

(57) ABSTRACT

Methods and apparatuses for sorting and isolating individual microparticles (e.g., cells) by bulk sorting groups of microparticles into groups containing one or more microparticle having a desirable characteristic (e.g., a label such as a florescent label, shape, size, etc.), and then sorting the individual microparticles with this desired characteristic individual particles.

12 Claims, 14 Drawing Sheets

(56) References Cited

U.S. PATENT DOCUMENTS

| | | | |
|---|---|---|---|
| 5,030,002 A * | 7/1991 | North, Jr. | G01N 15/1404 209/3.1 |
| 5,304,487 A * | 4/1994 | Wilding | B01J 19/0093 210/500.26 |
| 5,489,506 A | 2/1996 | Crane | |
| 5,750,015 A | 5/1998 | Soane et al. | |
| 5,837,200 A | 11/1998 | Diessel et al. | |
| 5,968,820 A | 10/1999 | Zborowski et al. | |
| 6,046,056 A * | 4/2000 | Parce | B01J 19/0093 204/400 |
| 6,120,735 A | 9/2000 | Zborowski et al. | |
| 6,467,630 B1 | 10/2002 | Zborowski et al. | |
| 6,778,724 B2 * | 8/2004 | Wang | H05H 3/04 385/16 |
| 6,815,664 B2 * | 11/2004 | Wang | B07C 5/34 250/251 |
| 7,160,730 B2 | 1/2007 | Bach et al. | |
| 7,392,908 B2 | 7/2008 | Frazier | |
| 7,425,253 B2 | 9/2008 | Voldman et al. | |
| 7,428,971 B2 | 9/2008 | Hirano et al. | |
| 7,452,725 B2 | 11/2008 | Leary et al. | |
| 7,745,221 B2 | 6/2010 | Butler et al. | |
| 7,807,454 B2 | 10/2010 | Oh et al. | |
| 7,820,427 B2 | 10/2010 | Unger et al. | |
| 8,349,277 B2 | 1/2013 | Azimi et al. | |
| 8,387,803 B2 | 3/2013 | Thorslund et al. | |
| 8,567,608 B2 | 10/2013 | Deshpande et al. | |
| 8,623,294 B2 * | 1/2014 | Asogawa | B01L 3/50273 422/50 |
| 8,658,418 B2 * | 2/2014 | Daridon | B01L 3/502761 435/287.2 |
| 8,691,164 B2 * | 4/2014 | Butler | B01L 3/502761 422/502 |
| 8,820,538 B1 | 9/2014 | Lin | |
| 9,522,344 B2 * | 12/2016 | Di Carlo | B01L 3/502761 |
| 2004/0233424 A1 | 11/2004 | Lee et al. | |
| 2006/0177348 A1 | 8/2006 | Yasuda et al. | |
| 2007/0178582 A1 | 8/2007 | Koser | |
| 2008/0138010 A1 | 6/2008 | Dou et al. | |
| 2008/0213821 A1 | 9/2008 | Liu et al. | |
| 2011/0030808 A1 | 2/2011 | Chiou et al. | |
| 2012/0103817 A1 | 5/2012 | Omori et al. | |
| 2012/0142018 A1 * | 6/2012 | Jiang | C12M 47/04 435/7.1 |
| 2012/0276641 A1 | 11/2012 | Dimov et al. | |
| 2013/0078733 A1 | 3/2013 | Holmes et al. | |
| 2013/0192958 A1 | 8/2013 | Ding et al. | |
| 2014/0008307 A1 * | 1/2014 | Guldiken | B01L 3/502761 210/748.05 |
| 2014/0087412 A1 | 3/2014 | Fouras et al. | |
| 2015/0367346 A1 | 12/2015 | Foster et al. | |
| 2016/0038940 A1 | 2/2016 | Babcock | |
| 2016/0167051 A1 * | 6/2016 | Collins | G01N 15/1031 435/325 |
| 2017/0030823 A1 * | 2/2017 | Wagner | G01N 15/1436 |

OTHER PUBLICATIONS

Lin; U.S. Appl. No. 15/377,822 entitled "Removable microparticle sorter cartridge," filed Dec. 13, 2016.

Lin; U.S. Appl. No. 15/318,542 entitled "Method and apparatus for particle sorting," filed Dec. 13, 2016.

\* cited by examiner

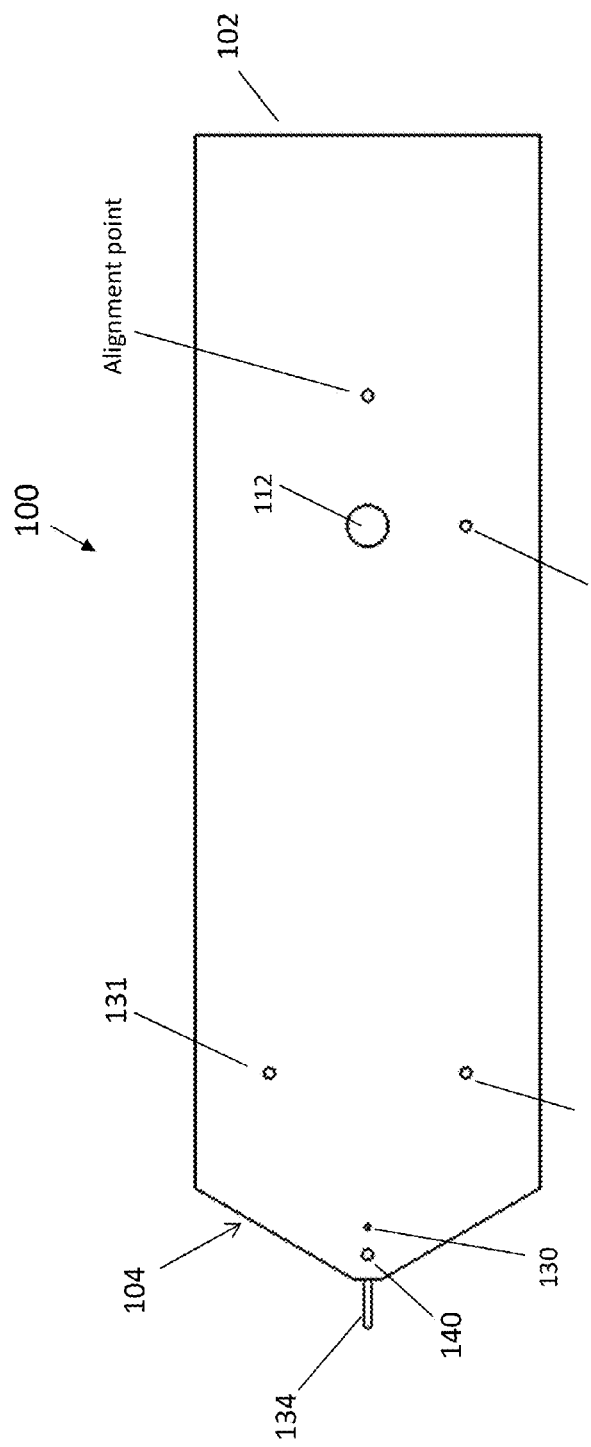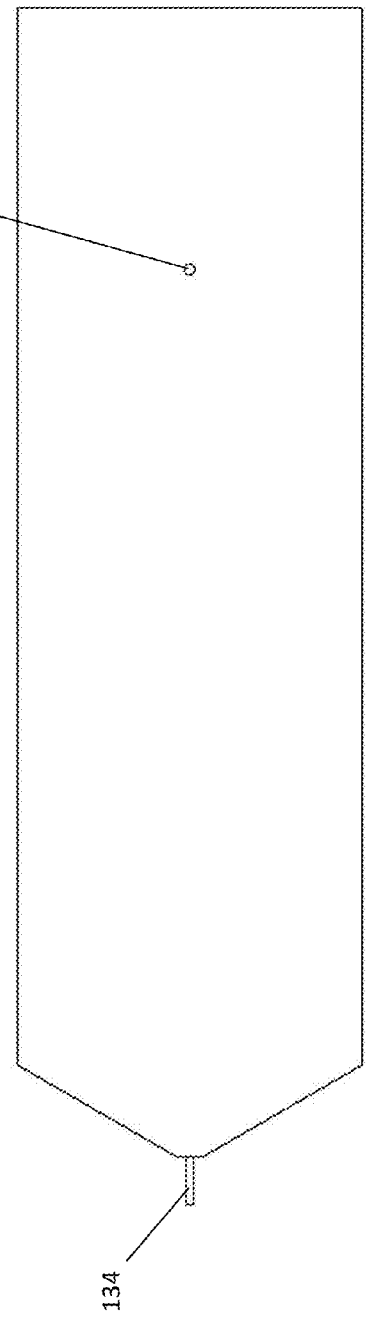

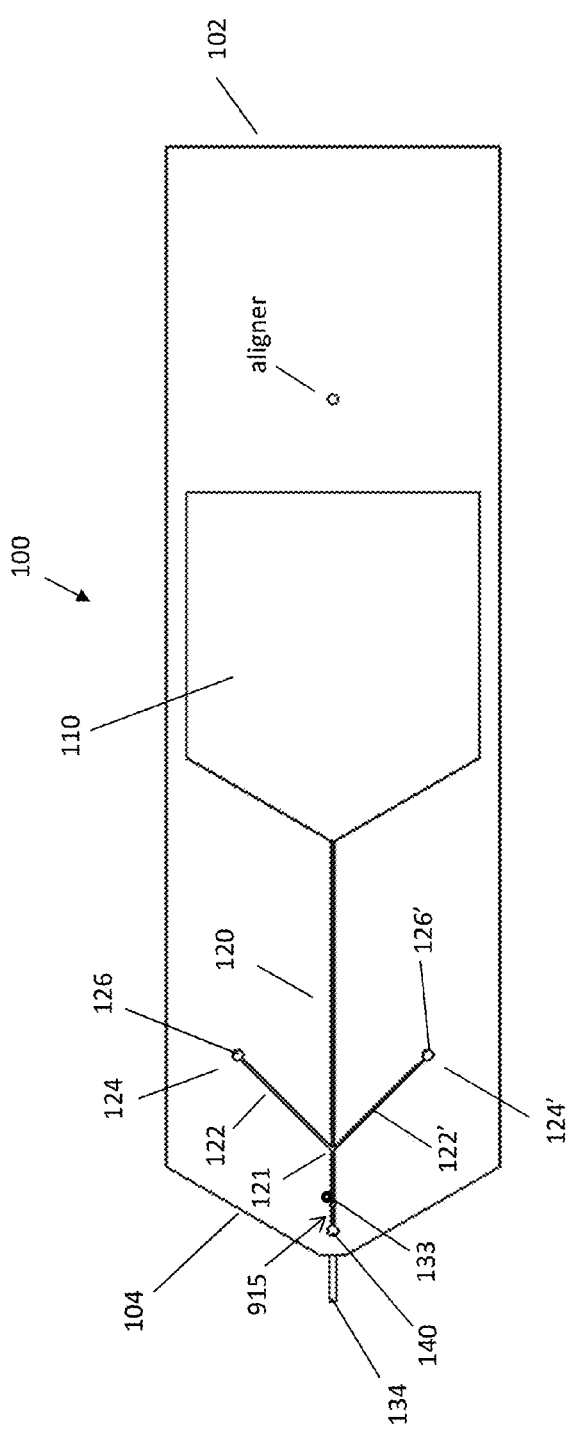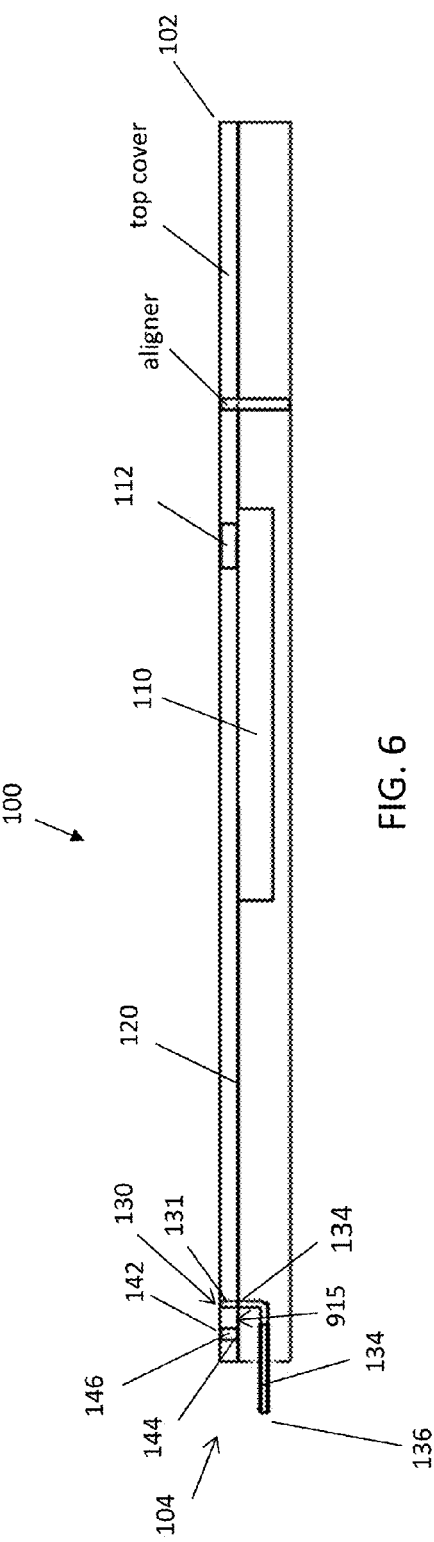

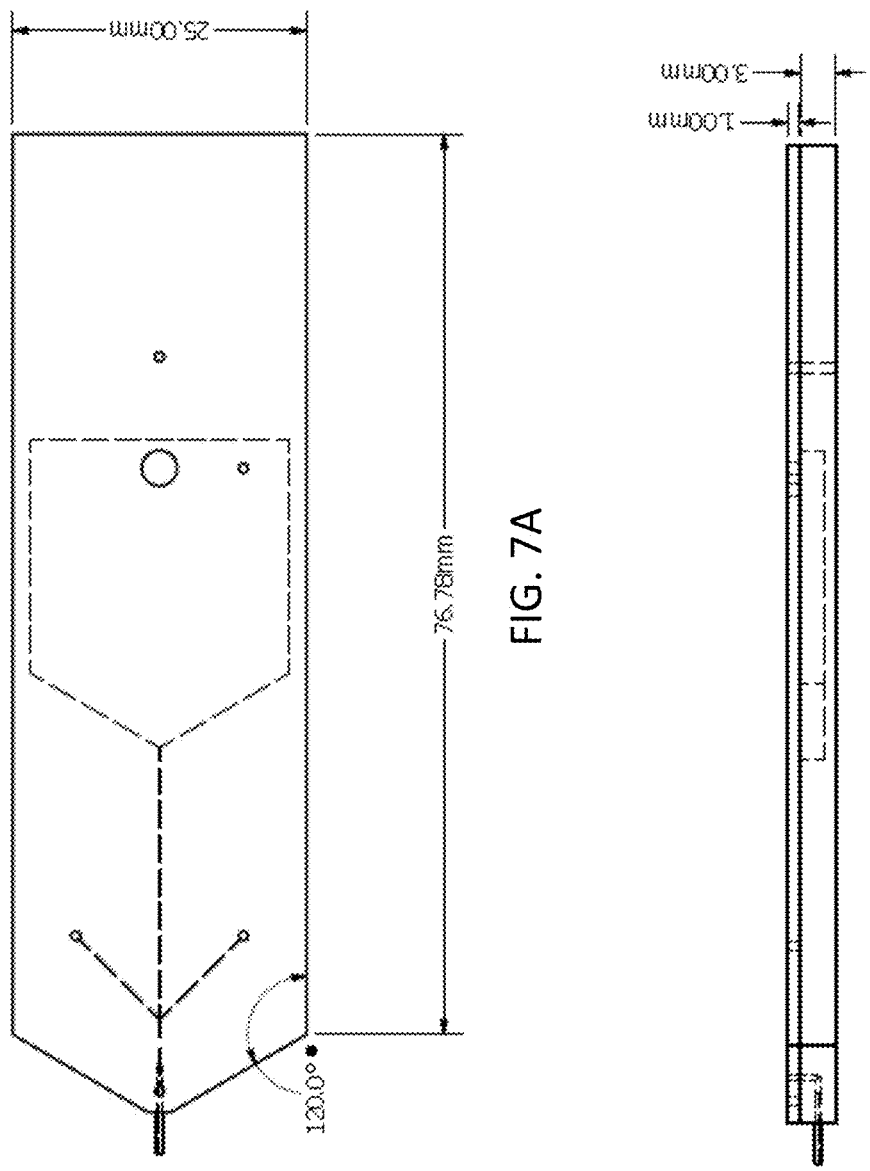

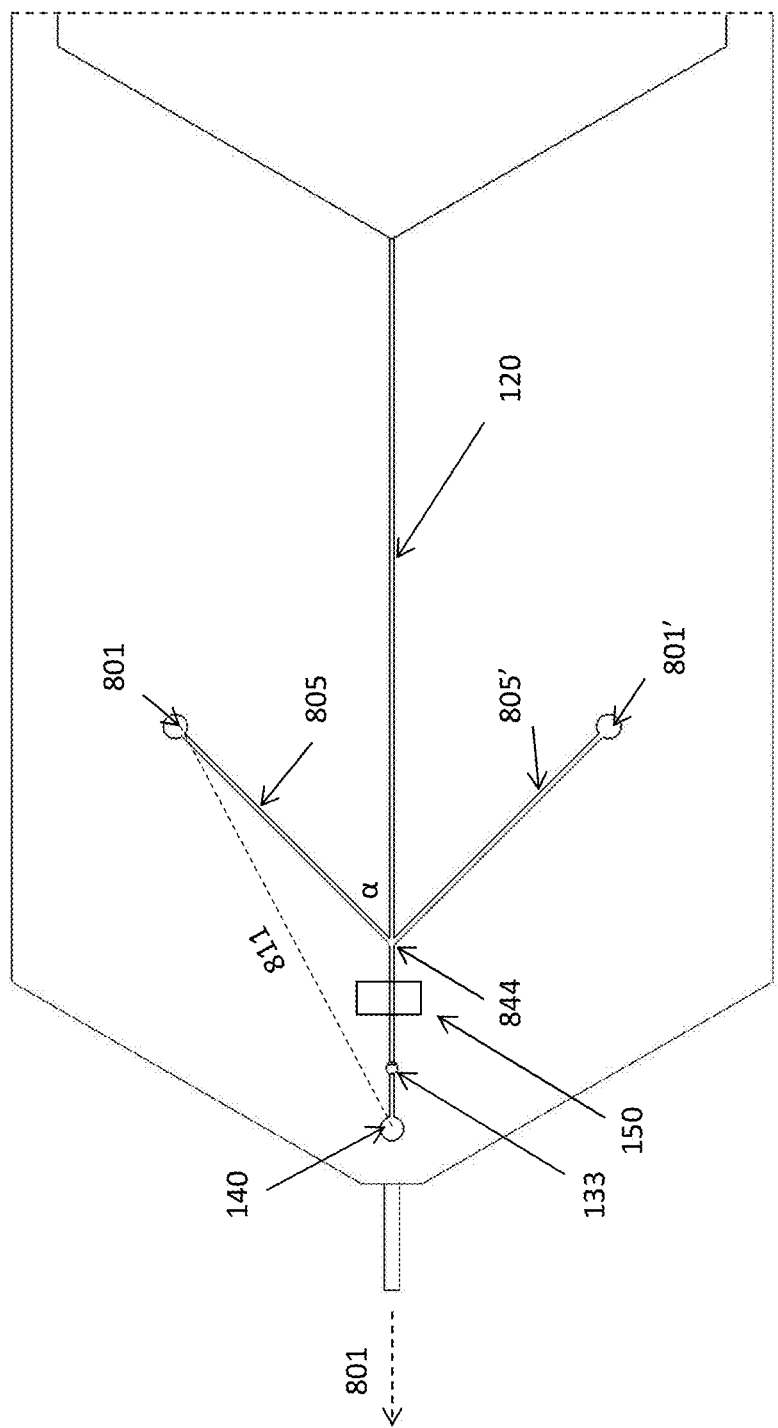

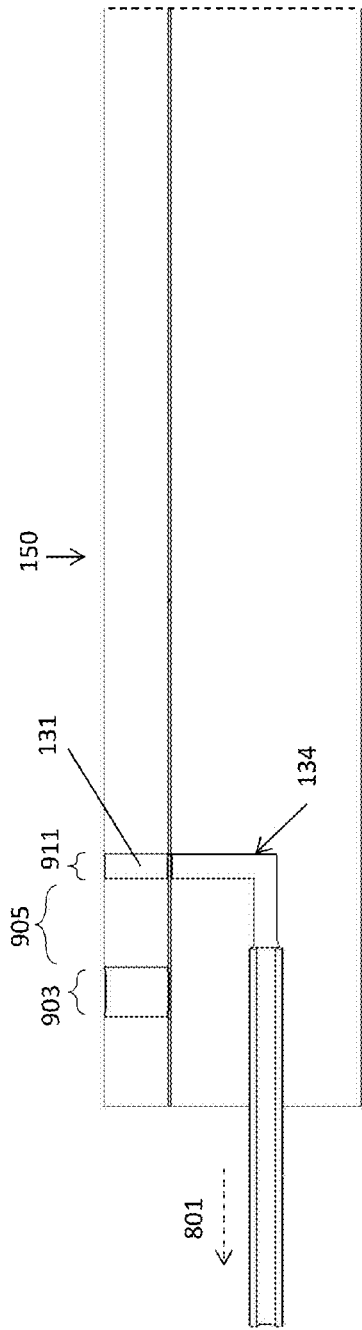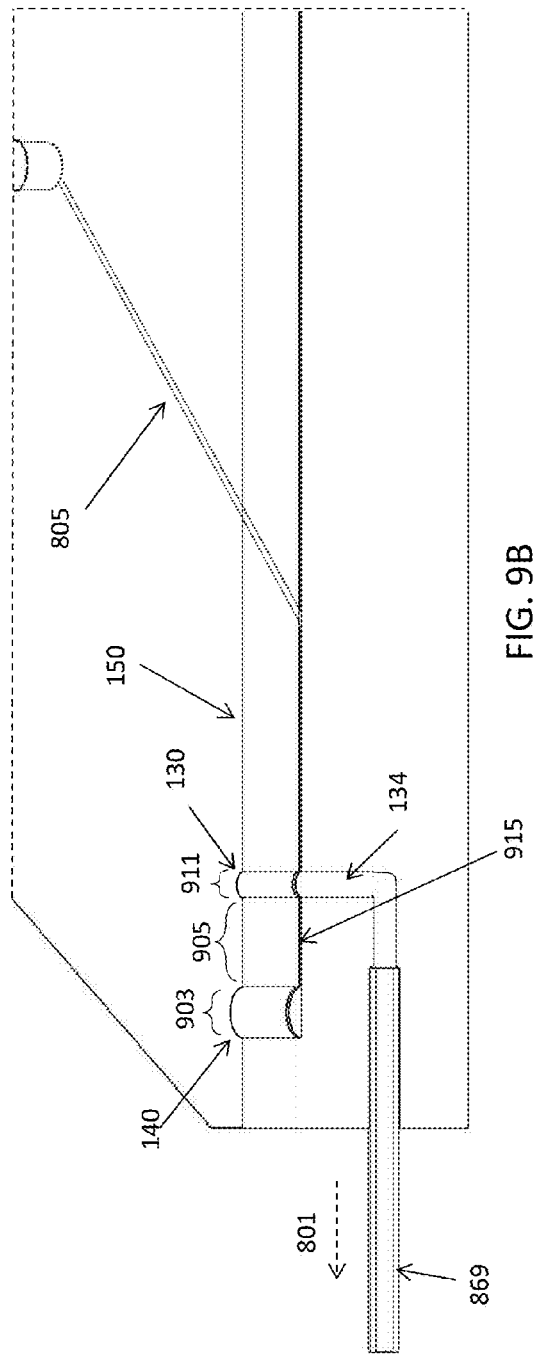

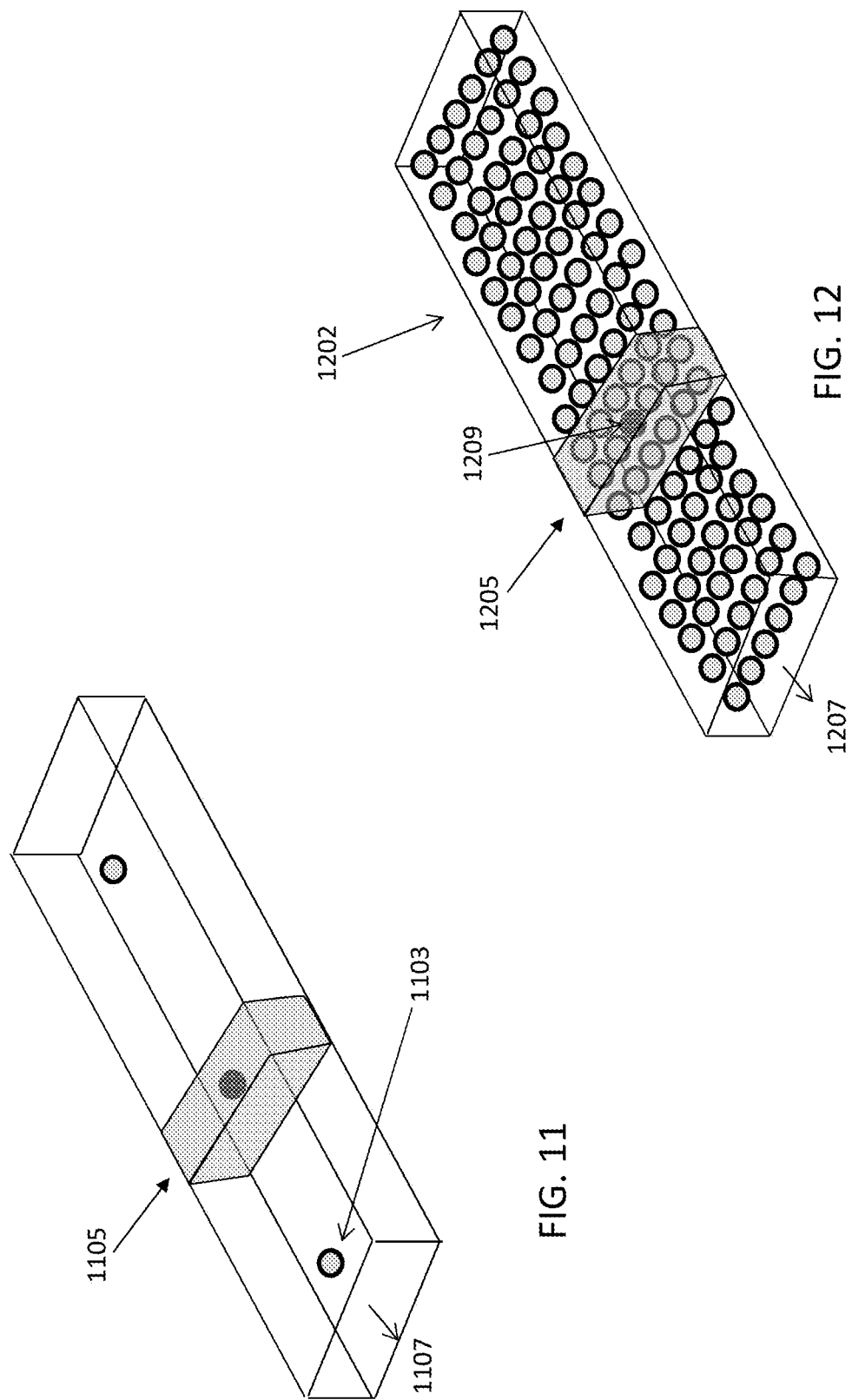

METHOD AND APPARATUS FOR BULK MICROPARTICLE SORTING USING A MICROFLUIDIC CHANNEL

CROSS REFERENCE TO RELATED APPLICATIONS

This application claims priority to U.S. Provisional Patent Application No. 62/323,162, filed on Apr. 15, 2016, titled "REMOVABLE MICROPARTICLE SORTER CARTRIDGE," which is herein incorporated by reference in its entirety.

This application also claims priority as a continuation-in-part of PCT Patent Application No. PCT/US2014/047152, filed on Jul. 18, 2014, titled "METHOD AND APPARATUS FOR PARTICLE SORTING," which is a continuation of U.S. patent application Ser. No. 14/216,185, filed on Mar. 17, 2014, titled "METHOD AND APPARATUS FOR PARTICLE SORTING," now U.S. Pat. No. 8,820,538. All of these patent applications and patents are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are disposable cartridges for microparticle (e.g., single cells) sorting apparatuses that automatically sort and dispensing microparticles.

BACKGROUND

Flow cytometry is used to differentiate various types of cells and other similar small particles. Conventional flow cytometers commonly comprise an optically-transparent flow cell, usually made of quartz, having a central channel through which a stream of cells to be individually identified is made to flow. Movement of the cell stream through the flow cell channel is hydrodynamically entrained to the central longitudinal axis of the flow cell channel by a cell-free sheath liquid that concentrically surrounds the cell stream and flows along with the cell stream as it passes through the flow cell channel. As each cell passes through a cell-interrogation zone of the flow cell channel, it is irradiated with a focused beam of radiation (e.g., laser). Upon impinging upon each cell, the laser beam is scattered in a pattern characteristic of the morphology, density, refractive index and size of the cell. Further, the spectral characteristics of the laser beam may act to excite certain fluorochromes associated with selected cells, as may be the case when a cell's DNA has been previously stained with such fluorochromes, or when a fluorochrome molecule has been conjugated with a selected type of cell, either directly or via an intermediate. Photodetectors strategically positioned about the optical flow cell serve to convert the light-scattered by each cell and the fluorescence emitted by the excited fluorochromes to electrical signals which, when suitably processed, serve to identify the irradiated cell. In addition to the light scatter and fluorescence measurements made on each cell, some flow cytometers further characterize each cell by measuring certain physical and/or electrical properties of each cell as it passes through the flow cell. The cells may be sorted to selectively remove and collect certain cells of interest (e.g., abnormal cells) from the cells that have already passed through the optical flow cell and have been identified. Various sorting techniques have been developed, including methods requiring forming and deflecting droplets containing one or a small number of cells.

For example, a cell-sorting component may include a piezoelectric device that acts to vibrate the flow cell to produce a stream of droplets from the cell-entraining sheath liquid exiting from the flow cell. Ideally, each droplet contains but a single cell that has been characterized as to cell type by the light-scatter and fluorescence measurements just made on such cell. Each droplet in the droplet stream is then electrostatically charged as it passes between a pair of electrically charged plates, and each charged droplet is selectively deflected (or not deflected) towards a collection container as it passes between a pair of electrostatically charged deflection plates, such plates being charged to a droplet-deflecting polarity only at a time to deflect droplets (and cells) of interest. The instantaneous polarity of the deflection plates is determined by a cell-characterization processor that processes the cell-measurement signals from the optical flow cell.

Such sorting of microparticles such as cells is very important in biological research and medical applications. The alternatively to flow cytometry is microfluidic sorting. Cells are flowed through a microfluidic channel in a single file while irradiated with a focused beam of radiation (e.g., laser). Fluorescent signals of the cell are detected by photodetectors. Cells are sorted into different microfluidic channel by some kind of physical force, such as by a gas impulse (e.g., U.S. Pat. No. 4,175,662, U.S. Patent Application Publication No. 2011/0030808), by an impulsive hydraulic force created by piezoelectric beam (e.g., U.S. Pat. No. 7,392,908), or by magnetostrictive gates (e.g., U.S. Pat. No. 7,160,730), by optical force (e.g., U.S. Pat. Nos. 8,426,209, 7,745,221, 7,428,971, U.S. Patent Application Publication No. 2008/0138010), by acoustic force (e.g., U.S. Pat. No. 8,387,803, U.S. Patent Application Publication No. 2013/0192958, U.S. Patent Application Publication No. 2012/0160746), by magnetic force (e.g., U.S. Pat. Nos. 8,071,054, 7,807,454 6,120,735, 5,968,820, 5,837,200), or by dielectrophoretic force (e.g., U.S. Pat. Nos. 8,454,813, 7,425,253, 5,489,506, U.S. Patent Application Publication No. 2012/0103817). In these examples, cells never leave microfluidic channel. In contrast to conventional flow cytometer which cells are sorted in the air (air sorting), microfluidic sorting is a sorting in fluidic flow (flow sorting). All microfluidic sorting devices run at much low pressure as compared to conventional flow cytometer. They are therefore gentler to cells. Also, microfluidic sorting devices in general are less complex and less expensive than conventional flow cytometer. However, most microfluidic sorting devices sorts at a rate which is typically two or more orders of magnitude lower than that of conventional flow cytometer. Recently, a next-generation microfluidics sorting apparatus using a high-frequency fluidic valve made of a silicon microchip, which can sort as fast as conventional flow cytometer (or potentially even higher than conventional flow cytometers) has been described (U.S. Patent Application Publication No. 2015/0367346).

Because microfluidic sorting is flow sorting. It does not generate droplet. Therefore, it cannot be used to capture single cell. In addition, the vast majority of known cell sorting mechanisms are focused on the sorting mixed cells into two or more populations. Droplet sorting by electrostatic force as described in U.S. Pat. No. 3,710,933 is the preferred mechanisms to deliver sorted individual cell to a predetermined location in real time. Unfortunately, droplet sorting is typically limited to delivery of sorted individual cells to a relative large area (e.g., more than 5 mm in diameter); for areas smaller than 5 mm in diameter, the deliver accuracy becomes very low because droplets typically travel at speed more than 1 m/s and to aim the droplets precisely to an area less 5 mm in diameter (e.g., using electrostatic force) is very difficult, particularly the speed of droplet is not constant. For example, currently available droplet cell sorters, such as BD ARIA III can sort individual cells directly into 96-well cell culture plate, in which the area of each well is about 6.5 mm in diameter, with accuracy of 70%. However, sorting individual cell into 384-well cell culture plate which is about 3 mm in diameter is not practical.

In contrast, there are commercially available technologies for delivering small volumes of liquids to precise locations. For example, the FLEXDROP (Perkin Elmer) is a liquid dispenser capable of delivering small amounts of liquid to a precise location having an area of less than 1 mm in diameter. Unfortunately, such liquid dispensers cannot sort cells.

Conventional systems that use flow cells or cartridges for processing microparticles typically rely on a single reusable cartridge for processing samples. Only after a certain amount of time is a sample cartridge replaced. This often means that a single cartridge processes hundreds if not thousands of samples before being replaced. In some instances, the flow cells or cartridges are never replaced until they fail. The reusable cartridges include a multitude of microliter or less volume channels, ports for connecting to the rest of the flow cytometry system, and reservoirs for retaining the sample as well as in some cases solvents, buffers, and/or biological media. In conventional systems, components including cartridges have to be flushed out prior to loading a new sample. While a flush cycle will remove the majority of sample and fluid medium from prior runs, over time residues may still build up not only within the channels but also along connection ports, inlets, and outlets. Having residue buildup within the cartridge may lead to inaccurate application of fluid flow through the cartridge channels. Residue buildup within the channels may also result in inaccurate microparticle detection and sorting. In addition to increased risk of contamination and decreased accuracy of sorting over time, current flow cytometry demands include processing large number of samples where washing the cartridge after each run may add up to large amount of time lost.

It would be advantageous to provide microfluidic sorting methods and apparatuses that may be used to sort both groups of separate microparticles and individual microparticles, rapidly and efficiently. It would also be useful to provide disposable cartridges for sorting that would eliminate the need for cleaning the sorting cartridge after each use. It would further be advantageous if the disposable cartridge sorter possessed a simple design that was also cost effective to manufacture in large quantities which make it feasible for the cartridges to be a one-time use only component of the microparticle sorting process.

SUMMARY OF THE DISCLOSURE

In general, described herein are apparatuses for sorting microparticles (e.g., cells) and methods of sorting microparticles.

In some variations, described herein are methods and apparatuses for sorting and isolating individual microparticles (e.g., cells) by bulk sorting groups of microparticles into groups containing one or more microparticle having a desirable characteristic (e.g., a label such as a florescent label, shape, size, etc.), and then sorting the individual microparticles with this desired characteristic individual particles.

For example, a method of bulk sorting and dispensing microparticles may include: passing a group of microparticles surrounded by fluid into a detection region of a first switch, wherein a plurality of microparticles within the group of microparticles are adjacently arranged within the detection region perpendicular to a direction of flow of the group of microparticles through the detection region; simultaneously examining the plurality of microparticles within the detection region to detect when at least one microparticle in the group of microparticles has a predetermined characteristic; passing the group of microparticles into a sample outlet flow path and dispensing the group of microparticles out of the sample outlet flow path when at least one microparticle in the group of microparticles has the predetermined characteristic, otherwise passing the group of microparticles through the first switch into a waste outlet flow path; isolating the at least one microparticle having the predetermined characteristic from the group of microparticles by passing the group of microparticles dispensed from the sample outlet through a second switch in a single-file arrangement through a detection region of the second switch, passing the at least one microparticle having the predetermined characteristic into a second sample outlet flow path of the second switch when the at least one microparticle is detected within a detection region of the second switch, and passing microparticles from the group of microparticles that do not have the predetermined characteristic into a waste outlet flow path of the second switch; and dispensing the at least one microparticle having the predetermined characteristic from the sample outlet of the second switch.

In general, the switches may be microfluidic sorting switches. For example, the switch may be a flow switch (as described in greater detail below), a gas impulse switch, a hydraulic force (piezoelectric beam) switch, a magnetostrictive gate (switch), an optical force switch an acoustic force switch, a magnetic force switch, a dielectrophoretic force switch, or the like.

When the switch is a flow switch, the flow switch may change a flow rate of the fluid surrounding the group of microparticles from a first flow rate to a second flow rate when at least one microparticle in the group of microparticles has the predetermined characteristic and is present in the switch. Changing the flow rate of the fluid surrounding the group of microparticles may comprise adding or subtracting fluid surrounding the group of microparticles. When flow switches are used, the resistance to fluid flow along the waste outlet flow path may be higher than the resistance to fluid flow along the sample outlet flow path.

For example, in some variations, simultaneously examining may include changing a flow rate of the fluid surrounding the group of microparticles from a first flow rate to a second flow rate when at least one microparticle in the group of microparticles has the predetermined characteristic and is present in the switch, and wherein passing the group of microparticles into the sample outlet flow path comprises passing the group of microparticles into the sample outlet flow path and dispensing the group of microparticles out of the sample outlet flow path when the fluid surrounding the group of microparticles is traveling through the switch at approximately the second flow rate, otherwise passing the group of microparticles through the switch into the waste outlet flow path when the fluid surrounding the group of microparticles is traveling through the switch at approximately the first flow rate.

In any of the methods described herein a group of microparticles may be sorted at the same time, and may be interrogated at the same time by a single (or multiple) detectors. For example, a laser scanning/illuminating detector may be used to illuminate the entire group of microparticles. For example, an illumination area for a detector may have a diameter that is greater than 2× the diameter that the average microparticle diameter (e.g., >2×, >3×, >4×, >5×, >6×, >7×, >8×, >9×, >10×, >11×, >12×, >13×, >14×, >15×, >20×, >25×, >30×, etc.) and/or a width that is greater than 2× the diameter that the average microparticle diameter (e.g., >2×, >3×, >4×, >5×, >6×, >7×, >8×, >9×, >10×, >11×, >12×, >13×, >14×, >15×, >20×, >25×, >30×, etc.). For example, the microparticles may refer to cells, and the average cell diameter may be approximately 10 µm (e.g. approximately: 5 µm, 10 µm, 12 µm, 15 µm, 20 µm, 25 µm, 30 µm, 35 µm, etc.), and the detector illumination (e.g., laser light) may have a diameter that is between 20 µm and 100 µm (e.g., between 10 µm and 500 µm, between 20 µm and 300 µm, between 30 µm and 400 µm, between 25 µm and 250 µm, etc., or any range there between), with similar or narrower widths.

Typically, the microfluidic channel including the detection region may be configured so that the microparticles pass through the detection region either single-file (when detecting and/or separating a single cells), or, as described herein, in groups of microparticles that are arranged abreast of each other, including side-by-side and above/below, approximately in a plane transverse to the direction of flow in the detection channel. For example, passing the group of microparticles may include passing multiple "layers" of cells through the flow switch at the same time for simultaneous inspection and sorting. Thus, multiple microparticles may be simultaneously illuminated, and the one or more (e.g., two, three, four, five, six) detectors configured to have a sensitivity such that if even a single microparticle in the group being concurrently or simultaneously illuminated have the desired property (e.g., florescence) then the entire group will be sorted and separated from the stream of microparticles passing through the detector region into the sample outlet flow path; other groups will instead by transmitted into a waste path (waste outlet flow path). The selected group of microparticles may then be examined either in smaller groups or as single microparticles. When a cartridge is used, either the same or a different cartridge may be used. For example, the same cartridge may re-circulate the microparticles transmitted to the sample outlet flow path back through the detection channel, but may limit the microparticles to smaller groups (e.g., by dilution, or by activating streamlining fluid paths as described below), or may direct the selected microparticles to a separate detection channel in the same cartridge. Alternatively or additionally, the microparticles may be loaded into a second cartridge in which they may be sorted individually or into smaller groups. Any of the apparatuses described herein may allow the user to select between group sorting and/or individual microparticle sorting. Toggling between group microparticle sorting and individual microparticle sorting may turn on/off streamlining fluid, and/or may change the pressure applied to the fluid in the detection region, and/or may alter the shape and/or size of the detection region and/or may change the path of selection. In some variations, group sorting vs. individual microparticle sorting may be selected based on the cartridge used.

As mentioned, any of the methods and apparatuses described herein may include multiple iterations of sorting, including isolating the at least one microparticle comprises passing the group of microparticles dispensed from the sample outlet through the second switch in which the second switch comprises the first switch.

In general, the apparatuses and methods described herein may include the use of a cartridge (e.g., removable and/or replaceable cartridge) for sorting and separating the microparticles. For example, passing the group of microparticles into the detection region may include passing the group of microparticles through a cartridge containing the switch, such as (but not limited to) a flow switch.

As mentioned, in general, the group of microparticles may be a group of cells. In some variations the microparticles may be clusters of cells. The microparticles may be any cell type, including blood cells (or other circulating cells, e.g., red blood cells, white blood cells, etc.) cancer cells, tissue culture cells, etc.

Microparticles may be selected/detected based on any appropriate predetermined characteristic (including combinations of predetermined characteristics). For example, the detected predetermined characteristic may be selected from one or more of: shape, size, and fluorescence intensity. Multiple detectors for the same characteristic, and/or for different characteristics may be used; for example, multiple florescent detectors may be used for different wavelengths of light, and/or for different sensitivity thresholds may be used.

In any of the methods and apparatuses described herein, the fluid surrounding the group of microparticles may be pressurized to a predetermined pressure or range of pressures.

In general, the methods and apparatuses described herein focus on the use of a flow switch to sort and isolate microparticles, however it should be understood that the group sorting and single-cell isolation methods described herein, as well as any of the other principles and techniques described, may be used with other sorting techniques (switches).

As mentioned, in general the methods and apparatuses described herein may sort groups of microparticles and may then repeat the sorting to isolate individual microparticles. Isolating may be done separately from the group sorting, or it may be done in combination.

For example, a method of bulk sorting and dispensing microparticles (e.g., using a flow switch), may include: passing a group of microparticles surrounded by fluid into a flow switch; changing a flow rate of the fluid surrounding the group of microparticles from a first flow rate to a second flow rate when at least one microparticle in the group of microparticles has a predetermined characteristic and is present in the flow switch; and passing the group of microparticles through the flow switch into a waste outlet flow path when the fluid surrounding the group of microparticles is traveling through the flow switch at approximately the first flow rate, or passing the group of microparticles through the flow switch into a sample outlet flow path and dispensing the group of microparticles out of the sample outlet flow path when the fluid surrounding the group of microparticles is traveling through the flow switch at approximately the second flow rate, wherein a static fluid pressure in the waste outlet flow path is lower than a static fluid pressure in the sample outlet flow path. The method may also include isolating the at least one microparticle having the predetermined characteristic from the group of microparticles by passing the group of microparticles dispensed from the sample outlet through an isolation flow switch, and changing a flow rate of fluid surrounding the at least one microparticle having the predetermined characteristic from a third flow rate to a fourth flow rate when the at least one microparticle having the predetermined characteristic is present in the isolation flow switch, whereby the at least one microparticle having the predetermined characteristic is dispensed from the isolation flow switch when the fluid surrounding the at least one microparticle having the predetermined characteristic is traveling through the isolation flow switch at approximately the fourth flow rate.

Isolating the at least one microparticle may include passing the group of microparticles dispensed from the sample outlet through the isolation flow switch in which the isolation flow switch comprises the flow switch. Isolating the at least one microparticle may include passing the group of microparticles dispensed from the sample outlet through the isolation flow switch in which the isolation flow switch comprises a second flow switch. Passing the group of microparticles may include passing the group of microparticles through a cartridge containing the flow switch. Any of the methods described herein may include degassing the fluid before it enters the switch (e.g., flow switch).

For example, a method of bulk sorting and dispensing microparticles may include: passing a group of microparticles surrounded by fluid into a first flow switch; changing a flow rate of the fluid surrounding the group of microparticles from a first flow rate to a second flow rate when at least one microparticle in the group of microparticles has a predetermined characteristic and is present in the first flow switch; passing the group of microparticles through the first flow switch into a waste outlet flow path when the fluid surrounding the group of microparticles is traveling through the first flow switch at approximately the first flow rate, or passing the group of microparticles through the first flow switch into a sample outlet flow path and dispensing the group of microparticles out of the sample outlet flow path when the fluid surrounding the group of microparticles is traveling through the first flow switch at approximately the second flow rate, wherein a static fluid pressure in the waste outlet flow path is lower than a static fluid pressure in the sample outlet flow path; and isolating the at least one microparticle having the predetermined characteristic from the group of microparticles by passing the group of microparticles dispensed from the sample outlet through an isolation flow switch comprising either a second flow switch or the first flow switch, and changing a flow rate of fluid surrounding the at least one microparticle having the predetermined characteristic from a third flow rate to a fourth flow rate when the at least one microparticle having the predetermined characteristic is present in the isolation flow switch, whereby the at least one microparticle having the predetermined characteristic is dispensed from the isolation flow switch when the fluid surrounding the at least one microparticle having the predetermined characteristic is traveling through the isolation flow switch at approximately the fourth flow rate.

As mentioned above, also described herein are removable (and in some variations disposable) cartridges that may be used with a flow cytometry apparatus and methods related to their use for sorting and retaining microparticles. These cartridges may be referred to as "sorting" cartridges. In general, the cartridges may have no moving parts yet may effectively separate microparticles such as cells based on a particular feature of those microparticles. The cartridges may be generally flat and thin (e.g., having a thickness that is less than 10 mm, less than 9 mm, less than 8 mm, less than 7 mm, less than 6 mm, less than 5 mm, between 0.1 mm and 10 mm, between 0.1 mm and 8 mm, between 0.1 mm and 6 mm, between 1 mm and 5 mm, etc.), particularly over the region containing the fluidics. The distal end region may generally be wedge or arrow-shaped (e.g., having sides that are at an angle of between 90 and 180 (e.g., between 91 and 150 degrees, between 100 and 140 degrees, etc.) relative to parallel lateral sides). The cartridges may be loaded through a port (e.g., opening) into which a sample solution including microparticles (e.g., cells) may be inserted; for example, the cartridge body may include a sample holder region in fluid connection with the fluidic network.

In general, the cartridges described herein may be used as part of a sorting apparatus (device or system) using a controlled flow switch to sort microparticles within the cartridge. A flow switch may be used to differentially sorting microparticles based on the flow rate of the microparticle (e.g., within a microfluidic channel in the cartridge) and/or the flow rate of the fluid surrounding the microparticle in the channel. Thus, in these variations the cartridge may be referred to as a flow switch cartridge. The cartridge, which is passive, typically does not include any active switches but is acted upon by directing fluid through one or more of the ports into the cartridge from the sorting apparatus. Thus, in general, the cartridges described herein may be coupled to a sorting apparatus so that one or more (e.g., a plurality of) ports on the cartridge interface with and connect to (e.g., via a gasket or other fluid-tight connection) complementary ports and fluidic lines in the sorting apparatus. The fluidic seals may be part of the apparatus and/or part of the cartridge. For example, in some variations, the fluidic seals are elastomeric seals. In some variations the seals are gaskets (e.g., O-rings, etc.). The gaskets may be integrated into the sorting apparatus for sealing against a surface (e.g., the top surface) of a cartridge.

The sorting apparatus (which may be referred to as a base unit) includes a cartridge receiver portion (e.g. a slot, a chamber, etc.) into which a cartridge may be inserted and held so that the various ports of the cartridge are coupled to fluid input/output lines, and so that an optical detection and/or imaging system (e.g., a laser imaging system, such as a side-scattering laser imaging system) may be used to detect when a cell is moving through an imaging region of the cartridge, e.g., within a microfluidics channel. The arrangement of the ports as well as the dimensions and positions of the fluidic channels within the fluid network in the cartridge may be critical for the operation of the cartridges as a fluidic switch for sorting.

For example, a fluidic network of the cartridge may be configured to switch as actively controlled by the sorting apparatus, so that the sorting apparatus may differentially direct fluid flowing through the cartridge (flow switch) based on the flow rate of the fluid within the cartridge. Further, these flow switches may be used in conjunction with an identification and control portion, such as an optical detection and/or imaging system, which can determine when a microparticle having predetermined properties is within a predetermined imaging region of the cartridge, so that the sorting apparatus can increase (or decrease) the flow rate of the fluid carrying the microparticle to sort the microparticle within the cartridge. As used herein, a cartridge may therefore act as a switch that sorts a material between two (or more) outputs from the cartridge based on the flow rate of material as it passes through the cartridge. In particular, the cartridges described herein may achieve differential flow sorting in conjunction with the sorting apparatus based on the differences between the resistance to flow through the outputs and different static fluid pressure at the interface between each output and a flow switch convergence region or sorting region in the cartridge.

A cartridge in conjunction with a sorting apparatus as described herein typically operates by using at least two outlets connected to different outlet channels (e.g., a waste flow path and a sample outlet flow path) exiting a sorting region, which may be referred to as a convergence or intersection region of the cartridge. During operation of the cartridge with the sorting apparatus, the outlet flow path and the waste flow path may have differential flow resistances and each outlet flow path may have a different static fluid pressure. In some variations at low flow rates (e.g., flow rates below a lower threshold value) flow out of the cartridge will be through a waste flow path and out of a first port that is coupled to a waste storage region of the sorting apparatus. The sorting apparatus may be configured to apply a low amount of suction (e.g., between a lower negative pressure value of 1 psi, 0.9 psi, 0.8 psi, 0.7 psi, 0.6 psi, 0.5 psi, 0.4 psi, 0.3 psi, 0.2 psi, 0.1 psi, etc., and a high negative pressure of 0.5 psi, 0.6 psi, 0.7 psi, 0.8 psi, 0.9 psi, 1 psi, 1.1 psi, 1.2 psi, 1.3 psi, 1.4 psi, 1.5 psi, etc. where the lower value is always less than the upper value, e.g. between 0.5 psi and 0.9 psi); at higher flow rates, e.g., flow rates above a higher threshold value, the flow out of the cartridge, e.g., carrying a sorted microparticle, may be through the outlet (droplet dispending) flow path and out of a droplet dispensing port. In particular, the waste (e.g. "low flow") flow path may have a static fluid pressure that is lower than the static fluid pressure at the outlet flow path (e.g., "high flow"), and the resistance to fluid flow along the outlet flow path to the droplet dispensing port may be lower than the resistance to fluid flow along the waste flow path coupled to the first (waste) port. Thus, the sorting apparatus may achieve sorting within the cartridge by changing the flow rate of fluid in the cartridge, and in particular in through a second port to the inlet flow path connected to the sorting region so that the material (e.g., the microparticle surrounded by the fluid) is switched from the waste flow path to the outlet flow path (e.g., sample outlet flow path).

Any of the cartridges described herein may contain both microfluidic structures and millifluidic structures to achieve cell sorting and cell dispensing at the same time when coupled to a sorting apparatus that is configured to operate the cartridge as a flow switch. For example, the flow resistance and/or static fluid pressures, as well as the flow rate of a fluid within the cartridge may be manipulated by microfluidic or macrofliudic structures within the cartridge and in some variations within the device.

In addition, any of the cartridges described herein may include features that prevent disruptions in the flow rate (e.g., preventing unintentional or uncontrolled changes in flow rate, such as turbulence) for fluid within the cartridge. Also, any of these systems may include a degasser to remove bubbles or to prevent bubble formation. Further, the flow paths through the flow switch may be configured to prevent or reduce turbulent flow.

For example, described herein are removable cartridge for a microparticle sorting apparatus, the cartridge comprising: an elongate body having a top surface, a bottom surface and thickness there between; a first port on the top surface near a distal end of the cartridge, wherein the first port lies in a longitudinal axis extending through a midline of the elongate body; a second port on the top surface, wherein the second port lies along the longitudinal axis and is separated from the first port by between 1 mm and 3 mm; an optional third port on the top surface spaced between 14-16 mm from the first port at an angle of between 20 and 60 degrees to the longitudinal axis; an optional fourth port on the top surface spaced between 14-16 mm from the first port at an angle of between −20 and −60 degrees to the longitudinal axis; a droplet dispensing port extending from the distal end of the cartridge between the top and bottom surfaces; and a fluidic network within the elongate body coupled to the first and second (and optional third and fourth) ports, the fluidic network comprising: a microfluidics channel extending through the elongate body between a sample holding region and a sorting region; an outlet flow path between the sorting region and the droplet dispensing port; a waste flow path extending through the elongate body between the sorting region and the first port; wherein a resistance to flow in the waste flow path is higher than a resistance to flow in the dispensing flow path (e.g., the dispensing outlet portion of the dispensing flow path) when a negative pressure of between 0.5 psi and 0.9 psi is applied to the first port.

In general, the first port may be referred to as a waste port, and may be located at or near the distal end of the cartridge and may couple to a waste line of the sorting device, e.g., through a gasket. Any of the ports described herein may be an aperture or opening of any appropriate dimension (e.g., round, oval, square, etc.). For example, the waste port may have a diameter of 0.8 mm or thereabouts (e.g., between 0.5 and 1.5 mm). Any of these ports may be flush with, recessed into, or project from (e.g., proud of) the top surface of the cartridge.

The second port may be referred to as an inlet port and may be coupled to a valved source of fluid (e.g., medium) within the sorting device when the cartridge is coupled to the sorting device. The (optional) third and fourth ports may be referred to as streamline fluid ports and may also be coupled to a source of fluid (e.g., medium) within the sorting device through a gasket or other seal. Depending on the configuration of the cartridge, the cell cartridge may contain only the first and second ports, without the third or fourth ports. For example, the cartridge optionally be operated without sheath liquid.

In general, the apparatuses described herein are configured in such way that the resistance to flow in the waste flow path is higher than a resistance to flow in the dispensing flow path (e.g., the dispensing outlet flow path portion of the dispensing flow path, downstream of the sorting region) when the cartridge is coupled to a sorting device. In order to achieve this, the cross-sectional area of waste flow path must be smaller than that of dispensing outlet flow path. This is particularly true when it is desirous to have a resistance to flow in the waste flow path is higher than a resistance to flow in the dispensing flow path (e.g., the dispensing outlet flow path portion of the dispensing flow path) when the cartridge is coupled to a sorting device and a negative pressure of between 0.5 psi and 0.9 psi is applied to the first port. It has been found that if, for example, the spacing between the first port and the second port is too far apart (e.g., greater than, e.g., 3-4 mm), then the resistance to flow in the waste flow path may be too high or may require an unduly high negative pressure, and the cartridge will not properly sort between the waste flow path and the dispensing flow path (e.g., the dispensing outlet flow path portion of the dispensing flow path), preventing operation of the device. Alternatively, other arrangements of the first, second, third and fourth ports may result in a resistance to flow in the waste flow path that is too low, resulting in air being drawn into the waste flow path from the dispensing flow path. Ideally, when a microparticle is not being sorted into the dispensing flow path (e.g. by the sorting device applying an increased flow into the second port and therefore the inlet flow path and through the sorting region), no fluid should pass out of the dispensing outlet flow path.

For example, it may be particularly advantageous for proper operation of the cartridge as described above when the minimum cross-sectional area of the waste flow path is less than the minimum cross-sectional area of the dispensing flow path. For example, the ratio of the minimum cross-sectional areas of the waste flow path and the inlet flow path may be between 0.05 and 0.5.

In any of these variations, the cartridge may include a sample loading port on the top surface in fluid communication with the sample holding region for loading fluid (with microparticles) into the cartridge sample holding region. The sample holding region may also include a venting port on the top surface that is in fluid communication with the sample holding region.

In general, the microfluidics channel may extend along the long axis of the cartridge, and may have any appropriate cross-sectional area and profile. For example, the channel may have a circular, rectangular, square, oval, or other cross-section. The microfluidics channel may have a cross-sectional area of less than 0.2 square millimeters (e.g., between 0.001 square mm and 0.2 square millimeters).

In general, the cartridge may include an inlet flow path between the second port and the sorting region. As mentioned, the inlet flow path may be used to apply fluid across the microfluidic channel path when a microparticle is detected within the microfluidic channel by a detector (such as a laser or other optical detector) scanning through an optically transparent region between the second port and the intersection region (e.g., detection region of the cartridge). The inlet flow path may be positioned opposite the outlet flow path, and the two flow paths may have similar or identical cross-sectional shapes and/or areas. These flow paths may be millifluidic rather than microfluidic. For example, these flow paths have cross-sectional area between about 5× and 100× (e.g., 10×, 20×, 30×, 40×, 50×, etc.) the cross-sectional area of the microfluidic channel.

Additional fluidic channels may be used for guiding and/or centering the sample fluid and/or particles such as cells within the sample fluid as it travels down the microfluidic channel towards the sorting region. For example, any of these cartridges may include a first streamlining flow path extending through the elongate body between the third port and the microfluidics channel, when included, wherein the first streamlining flow path intersects the microfluidics channel at an intersection region; and a second streamlining flow path extending through the elongate body between the fourth port and the microfluidics channel, wherein the second streamlining flow path intersects the microfluidics channel at the intersection region.

The optically transparent region (detection region) is typically between the sorting region where the microfluidics channel intersects the inlet flow path, and the intersection region (e.g., between 0.5 and 10 mm from the sorting region).

The sample holding region may generally be between the top and bottom surfaces.

The droplet dispensing port typically extends from the distal end (or distal end region) of the cartridge, and thus may be at 90 degrees from the other ports. The droplet dispensing port may comprise a cannula extending from the distal end of the cartridge. For example, the droplet dispensing port may comprise a cannula extending from the distal end of the cartridge and further the distal end of the cartridge may be positioned between a pair of sidewalls that are angled between 95 and 160 degrees (e.g., between about 110 to 150 degrees, etc.) relative to a long axis of the cannula.

In any of these variations, the resistance to flow in the waste flow path may be between about 2 and about 40 times of the resistance to flow in the dispensing outlet flow path.

For example, a removable cartridge for a microparticle sorting apparatus may include an elongate body having a top surface, a bottom surface and thickness there between; a first port on the top surface near a distal end of the cartridge, wherein the first port lies in a longitudinal axis extending through a midline of the elongate body; a second port on the top surface, wherein the second port lies along the longitudinal axis and is separated from the first port by between 1 mm and 3 mm; a third port on the top surface spaced between 14-16 mm from the first port at an angle of between 20 and 60 degrees to the longitudinal axis; a fourth port on the top surface spaced between 14-16 mm from the first port at an angle of between −20 and −60 degrees to the longitudinal axis; a droplet dispensing port extending from the distal end of the cartridge between the top and bottom surfaces; a sample holding region configured to hold a microparticle-containing fluid; and a hybrid microfluidics and millifluidics network within the elongate body coupled to the first, second, third and fourth ports, the microfluidics and millifluidics network comprising: a microfluidics channel extending through the elongate body between the sample holding region and a sorting region; an inlet flow path between the second port and the sorting region; an dispensing outlet flow path between the sorting region and the droplet dispensing port; a waste flow path extending through the elongate body between the sorting region and the first port; a first streamlining flow path extending through the elongate body between the third port and the microfluidics channel, wherein the first streamlining flow path intersects the microfluidics channel at an intersection region; and a second streamlining flow path extending through the elongate body between the fourth port and the microfluidics channel, wherein the second streamlining flow path intersects the microfluidics channel at the intersection region; wherein a resistance to flow in the waste flow path is higher than a resistance to flow in the dispensing flow path when a negative pressure of between 0.5 psi and 0.9 psi is applied to the first port.

The disposable sorting cartridges described herein are able to sort samples containing a mixture of microparticles based on a pre-determined characteristic. Application of fluidic and gaseous forces is used to aid with channeling and collecting microparticles with specific characteristics. While it is possible to move almost anything by applying the right amount of force, it is unexpected that applying only a small amount of positive and negative forces within a fairly simple network, could result in a precise way of sorting microparticles such as cells, as is possible with the cartridges described herein.

In general, as the sample travels down the main flow path of the disposable sorting cartridges, the individual microparticles begin to separate from one another and travel singly down the main flow path. Side flow channels disposed symmetrically about the main flow path are connected to reservoirs maintained within the corresponding flow cytometry apparatus may provide additional control of the fluidic flow rate to ensure that the microparticles travel down the main flow path as single microparticles.

A detector region along the main flow path interrogates the microparticles passing through to determine if each microparticle possess or does not possess a particular characteristic. Signals from the detector are analyzed by the sorting device (which may also be referred to herein as a flow cytometry apparatus). If the microparticle(s) possesses the pre-determined characteristic, the flow cytometry apparatus controls will initiate protocols to retain the microparticle. In this case, as the desired microparticle moves past the detector, it will encounter the sorting region. The second port (an inlet port) is fluidly attached to a reservoir maintained within the flow cytometry apparatus where the reservoir may provide additional fluid flow or positive pressure timed so that flow is initiated when or after the microparticle is detected, specifically driving the microparticle into the dispensing flow path (e.g., the dispensing outlet flow path portion of the dispensing flow path) and therefore the droplet dispensing port; when no desired particle is detected, the flow cytometery apparatus does not apply fluid flow through the second port into the dispensing flow path, and instead flow continues from the microfluidic path into the waste flow path which is couple to the first port and may receive negative pressure from the flow cytrometry apparatus, removing the waste material from the cartridge. The second port is in fluid connection with the dispensing flow path that has a cross sectional area greater than that of the main microfluidic channel (flow path).

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 4A is a top view of a removable cartridge.

FIG. 4B is a bottom view of the cartridge of FIG. 4A.

FIG. 5 is an X-Y plane cross sectional view of the cartridge of FIGS. 4A and 4B.

FIG. 6 is a Y-Z plane cross sectional view of the cartridge of FIGS. 4A and 4B.

FIG. 7A illustrates another example of a cartridge including exemplary dimensions.

FIG. 7B is a side view of the cartridge of FIG. 7, including exemplary dimensions.

FIG. 8 is an enlarged view of a section through the cartridge of FIG. 7A, showing a portion of the fluidic network including the sorting region and the streamlining flow channels.

FIG. 9A is a section through the side of the distal end of a cartridge as described herein.

FIG. 9B is an isometric view of a section such as the one shown in FIG. 9.

FIG. 11 shows an example of a microfluidics channel in which microparticles (e.g., cells) are passed in single-file for individually sorting.

FIG. 12 shows an example of a microfluidics channel in which microparticles are passed in bulk, in groups microparticles for simultaneous sorting, as described herein.

DETAILED DESCRIPTION

Described herein apparatuses and methods for using microfluidics to sort both groups of separate microparticles and individual microparticles. Also described herein are cartridges that may be used for sorting groups and/or individual microparticles (e.g., cells).

Although the devices and apparatuses described herein may sort based on flow rate, for example, using a flow switch, in some variations these devices and apparatuses described herein are not limited to the use of flow switches. The majority of the examples described herein are provided in the context of flow switches, but it should be understood that other sorting techniques (e.g., other microfluidic sorting techniques) may be used.

For example, the majority of the cartridges described herein are microfluidic sorting cartridges for sorting groups of microparticles and/or sorting and isolating individual microparticles, and may include a flow switch. For example, described herein are cartridges for microparticle sorting devices that may sort within the cartridge based on the flow rate (speed and direction) of the fluid surrounding the microparticle. The cartridges described herein may use a balanced arrangement of fluid paths having controlled dimensions, including path length, diameter (cross-sectional area) and relative locations to sort microparticles passing from a sample holding region and through a central microfluidics channel.

The cartridges described herein are adapted to operate as a portion of flow switch similar to that described, for example, the inventors issued U.S. Pat. No. 8,820,538, filed on Mar. 17, 2014, titled "METHOD AND APPARATUS FOR PARTICLE SORTING" and herein incorporated by reference in its entirety. The flow switch may be divided between a removable cartridge and a flow cytometry apparatus ("sorting device") that can receive the cartridge. The interface between the cartridge and the sorting device is important in allowing operation of the flow switch. In particular, the arrangement of the ports on a single (e.g., "top") surface that is 90 degrees from the droplet dispensing port and the arrangement of the hybrid microfluidics and millifliudics network within the cartridge may be important. Surprisingly, arrangements outside of those described herein have been found to be unsuccessful, because the requisite balance between the resistances to flow between the waste flow path and the dispensing flow path, and/or the static fluid pressures within these flow paths during operation of the sorting device are not within a range that permits operation of the flow switch.

Figure 1:
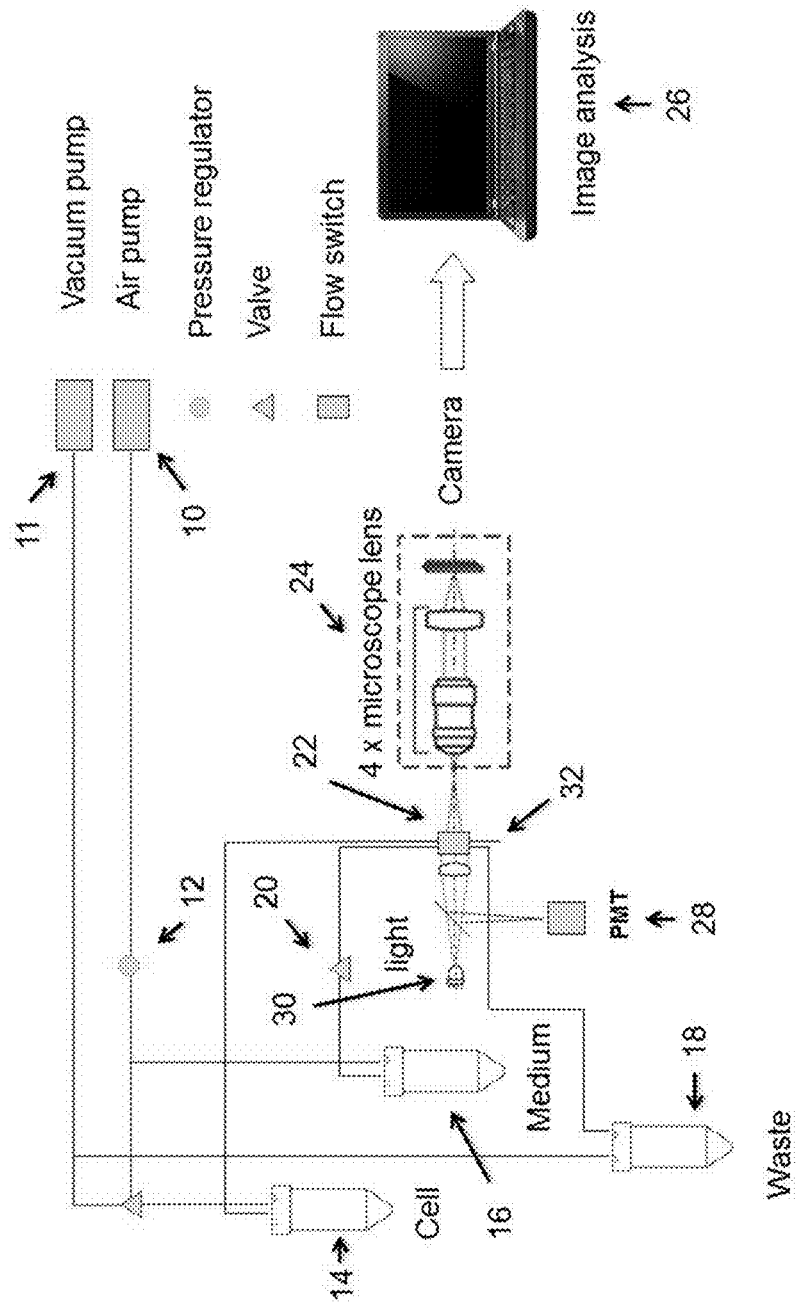
FIG. 1 schematically illustrates a sorting apparatus that does not include a cartridge.
Figure 2B:
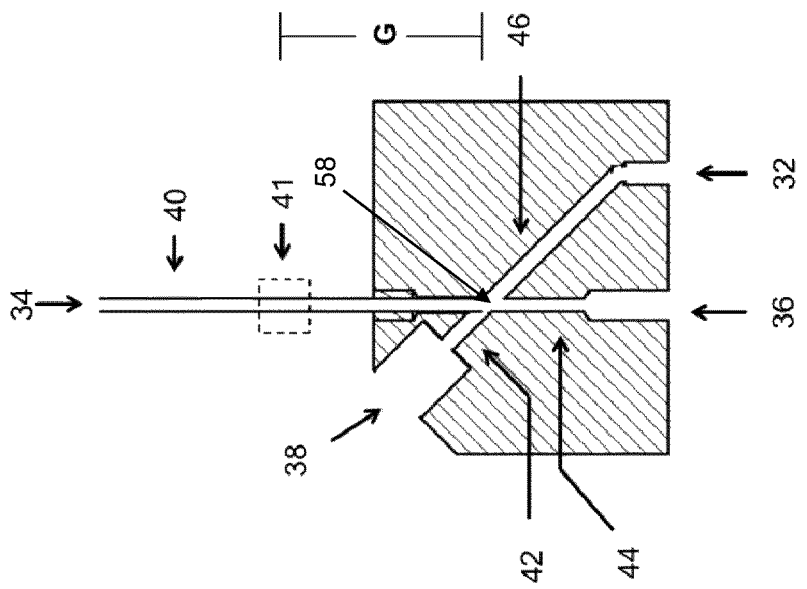
FIG. 2B is a cross-section through the flow switch of FIG. 3A.
Figure 2A:
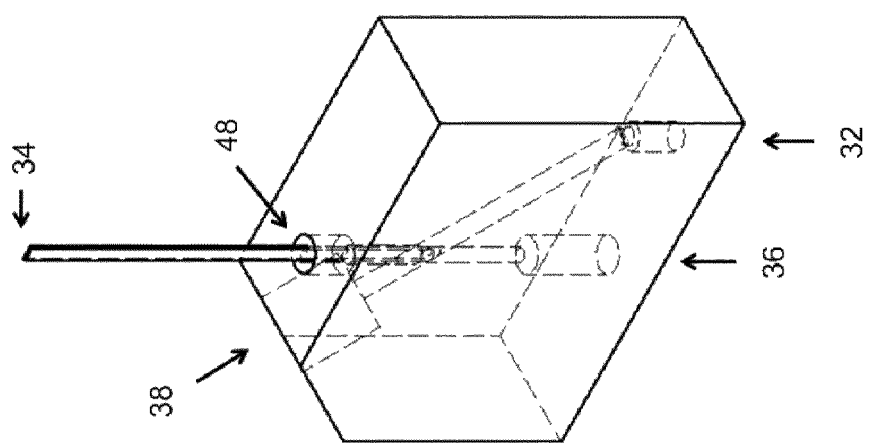
FIG. 2A illustrates one embodiment of monolithic flow switch.
Figure 3:
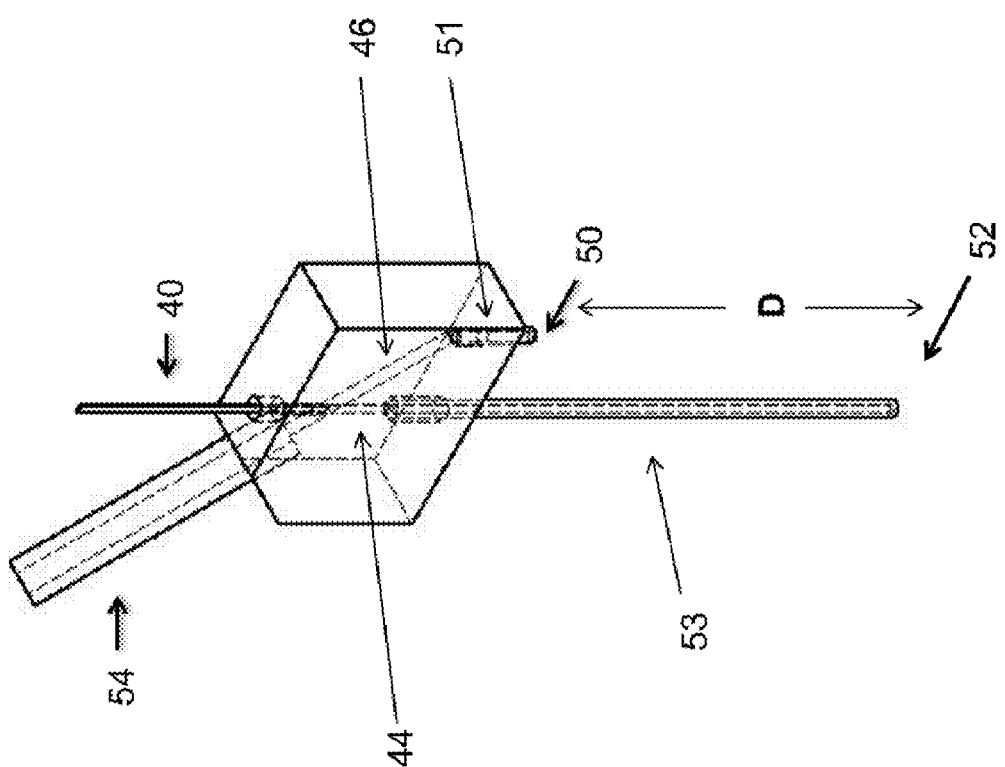
FIG. 3 shows another variation of a flow switch such as the one shown in FIGS. 2A and 2B, with source, waste and dispensing channels (tubes) shown attached.

FIGS. 1-3 illustrate the microfluidics sorting system, including the flow switch described in U.S. Pat. No. 8,820, 538. Both the integrated system and the cartridges described herein use alternating fluidic flow paths which contain at least one inlet and at least two outlets, wherein alternating fluidic flow path is achieved by changing flow rate into the flow switch system. In some variations the flow switch includes at least two inlets and at least two outlets. One flow path (e.g. waste flow path) may be maintained at low flow rate wherein the pressure in one flow outlet is kept lower than that in the other flow outlet. A lower pressure may be maintained in one flow outlet as compared to the other flow outlet, for example, by lowing the opening of one flow outlet as compared to that of the other flow outlet. The other flow path may be maintained at high flow rate wherein flow resistance in one flow outlet is lower than that in the other flow outlet.

In general, the apparatus (e.g., cartridges) described herein may be used to sort any appropriate microparticles, including microparticles that are single cells, clusters of cells, inorganic particles, or any other object, typically of small size (e.g., <10 µm, <20 µm, <50 µm, <100 µm, <200 µm, less than 0.5 mm, <1 mm, <100 µm. etc.).

The sorting may be controlled by a detector that detects the microparticles in the fluid supplied into the cartridge, which may be referred to as source fluid. The microparticle detection sub-system may continuously or discretely monitor the source fluid before or as it flows in the cartridge to determine when a microparticle having one or more predetermined characteristics is within a target detection region of the cartridge. For example, the system may be configured to sort based on cell shape, cell size, cell morphology, of a label on/applied to the cell (e.g., fluorescence intensity of a fluorescently labeled cell). Once a microparticle having the desired characteristics is identified, it may be sorted by changing the flow rate of the solution around the microparticle so that it is directed to the dispensing outlet (e.g., a fast-flow outlet) instead of the tonic, "waste" outlet (e.g., low-flow outlet). The sample inlet into the (or within the) cartridge may be configured so that microparticles having predetermined characteristics occur discretely within the detection region (e.g., field of view of the microparticle detection sub-system). The sample inlet channel may be adapted or configured to permit only single microparticles though at a time, for example, by including a narrow channel region, and particularly the region being viewed by the microparticle detection sub-assembly. Alternatively or additionally, the sample fluid containing the microparticles may be diluted such that the occurrence of microparticles within the field of view is relatively uncommon (e.g., probabilistically low).

As mentioned, the cartridges described herein typically have microfluidic channel extending down the long axis of the cartridge that may be microfluidic channels. One or more inlet fluidic paths may intersect the microfluidic path at a sorting region. Fluid (sample fluid) may be driven within the flow path at a rate that is determined by the sorting device when the cartridge is coupled thereto, in part, by a pressure, e.g., air pressure provided by an air pump. The system may include feedback regulating the fluid pressure within the different regions of the cartridge and/or just the sorting device, including in particular the source fluid input.

In general, differential switching based on fluid flow rate may be achieved within the cartridge by including one waste fluidic path that has a fluidic resistance that is higher than the fluidic resistance of the dispensing fluidic paths. In addition the static water pressure at the region of the outlet flow path near the sorting region of the cartridge, e.g., immediately after entering an outlet pathway, may be different. For example, one outlet may have an opening (connecting to a port such as the first, waste, port, or the droplet dispending port) that is lower than the opening of the other outlet(s), resulting in a different static water pressure between the outlets of the cartridge.

In general, the cartridges described herein may be made of any appropriate material, including glass, polycarbonate, a combination of both, or from some other material. Any port of the cartridge described may have a round, oval, triangular, rectangle, or other shaped cross section.

FIG. 1 shows an example of the flow switch described in U.S. Pat. No. 8,820,538. In FIG. 1, microparticles, such as cells, are stored in bottle 14. Bottle 16 contains only liquid, and in the case of cell sorting, it contains cell medium or saline buffer such as phosphate buffered saline. Both bottles are pressurized by a micro-diaphragm gas pump 10. The pressure in bottle 14 and bottle 16 is regulated by pressure regulator 12. The pressure in bottle 14 and bottle 16 may be 0-30 psi. In one embodiment, the pressure in bottle 14 and bottle 16 is 2 psi. Bottle 14 is directly connected to one inlet of the flow switch 22 through silicone tube. When bottle 14 is pressurized, liquid in bottle 14 will constantly flow through silicone tube into flow switch 22. Bottle 16 is connected to the other inlet of flow switch 22 through silicone tube. The flow of liquid from bottle 16 to flow switch 22 is controlled by solenoid valve 20. When cells are flowed through the flow switch 22, they are visualized through camera coupled with microscope lens 24. The fluorescence intensity of the cell is measured by photomultiplier tube (PMT) 28 at the same time. If the cell does not meet the preset criteria, such as the size, shape and fluorescence intensity, solenoid valve 20 remains closed. The cell will flow out of flow switch into waste bottle 18. If the cell meets the preset criteria, solenoid valve 20 opens for short period of time. Medium will flow into flow switch 22. The majority of medium will flow out of sample channel 32. The flow of medium will carry the targeted cell out of the nozzle of the sample channel 32. Thus sorting and dispensing a single cell is achieved at the same time.

Successful sorting and dispensing cells in this example may depend on the specific design of this monolithic flow switch. Referring to the schematic illustration of FIG. 2A, in this example a flow switch has two flow inlets 34 and 38, connected to inlet flow paths 40 and 42, respectively, and two flow outlets 32 and 36, connected to the flow outlet paths 46 and 44, respectively, of the flow switch. The inlet and outlet flow paths all converge in a common convergence region 58. Inlet 34 is connected to bottle 14 and inlet 38 is connected to bottle 16. Microparticles flow into flow switch through a sample inlet flow path 40. Additional fluid flows through a flush inlet flow path 42 to alter the flow rate of fluid surrounding the microparticles in the flow switch from low flow rate to high flow rate. Outlet 32 is connected to sample channel 51 and outlet 36 is connected to waste channel 53 which leads to the waste container (bottle) 18. The flow switch contains both microfluidic flow channels and macrofluidic flow channels. Sample inlet flow path 40 is a microfluidic channel. Flush inlet flow path 42, waste flow path 44 and sample outlet flow path 46 are macrofluidic channels. In one embodiment, sample inlet flow path 40 is made of glass capillary with rectangle cross-section with the dimension 30 µm×300 µm (H×W). In one embodiment, flush inlet flow path 42, waste flow path 44 and sample outlet flow path 46 are made from a single piece of polycarbonate. The cross-sections of flush inlet flow path 42, waste flow path 44 and sample outlet flow path 46 may be circular. In one embodiment, the diameters of flush inlet flow path 42 and sample outlet flow path 46 are 400 µm. The diameter of waste flow path 44 is 300 µm. Sample inlet flow path 40, flush inlet flow path 42, waste flow path 44 and sample outlet flow path 46 are converged at the center of flow switch 58.

To achieve cell sorting, there must be as least two flow outlets: one for wanted (sample) cells and the other for unwanted (waste) cells. An easy way to change flow path between two flow outlets is to change the flow resistance between two flow outlets through valves. For example, there are valves A and B in the flow path A and B respectively. To let the liquid to flow only through flow path A, and not path B, simply turn valve A in the path A on and turn valve B in the path B off. However having two controllable valves in two flow path outlets creates large dead volume. This is why such a method is rarely used in cell sorting apparatus. Traditionally, cell sorting was achieved by keeping both flow outlet paths open and by applying certain amount of external physical forces, such as mechanical force, acoustic force, hydraulic force, optical forces, magnetic force, dielectrophoretic force, or electrostatic force as described in the background section, directly to a targeted cell to force it to move from one flow path to the other flow path. In contrast, in the flow switches described herein, both flow outlet paths are open (FIG. 3), and no external force is used to switch flow paths. Switching between two flow paths may be achieved by simply changing flow rate into the flow switch. In FIG. 3, which shows another example of a monolithic flow switch, cells flow into flow switch through sample inlet flow path 40. When medium flow into flow switch through silicone tube 54 is blocked by valve 20, cell flow is the only flow into the flow switch. Normally cells can flow out of the two outlets of flow switch through either waste flow path 44 or sample outlet flow path 46. However, the flow switch is assembled in such way that the waste channel opening 52 is below the sample channel opening 50. The distance between the waste channel opening 52 and the sample channel opening 51 is D in FIG. 3. In one embodiment, D equals 70 mm. The flow rate of cell through microfluidic channel 40 is low. In one embodiment, the cell flow rate is 20 µl/min. Because cross-section area of the waste channel 53 is much larger than the cross-section area of sample inlet flow path 40, the pressure drop created by cells flowing through waste channel 53 is typically smaller than the static water pressure D in FIG. 3. Therefore, cells only flow into waste flow path 44 and finally into waste. No cells will flow into sample outlet flow path 46 and out of sample channel 51. While cells are flowed through the sample inlet flow path 40, they are inspected by a digital high speed camera and their fluorescence intensities are measured by PMT through an inspection window 41 (FIG. 2B). If the cell meets the preset criteria, such as size, shape and fluorescence intensity, valve 20 opens after a certain amount of delay, and medium flows into flow switch through silicone tube 54. The flow rate of medium into the flow switch is much larger than that of cell flow. In one embodiment, the medium flow rate is 500 ul/min. The diameter of silicone tube 54 is larger than that of the waste channel 53. In one embodiment, the diameter of silicone tube 54 is 0.762 mm whereas the diameter of silicone tube 52 is 0.30 mm. The large flow through silicone tube 54 into flow switch will change the flow pattern. A majority of medium will flow into sample outlet flow path 46 and out of sample channel 51 because flow resistance through the sample channel 51 is lower than that through waste channel 53. Movement of medium into sample outlet flow path 46 will also move targeted cell into sample outlet flow path 46 and out of the sample channel 51. Valve 20 only opens long enough so that the targeted could be dispensed out of the sample channel 51. In one embodiment, valve 20 opens for 25 ms. Thus single cell sorting and dispensing is achieved by changing the flow rate in the flow switch from 20 ul/min to 520 ul/min. Because target cell is dispensed out of the flow switch as a droplet through the sample channel 51, the location of dispensed droplet can be precisely controlled to accuracy less than 1 mm.

When valve 20 is closed, the pressure in waste flow path 44 is lower than that in sample outlet flow path 46 because the opening 52 of waste channel 53 is lower than the opening 50 of sample channel 51. Lower pressure in waste flow path 44 as compared to sample outlet flow path 46 may also be achieved by connecting the waste bottle 18 to a vacuum pump without setting opening of waste channel 53 to be lower than the opening of sample channel 51.

Removable Microparticle Sorter Cartridge

In general, the removable microparticle sorter cartridges described herein includes a network of fluidic channels etched into a thin piece of material. Suitable materials may include plastic, glass, or other transparent polymers. In some examples, the fluidic channels are etched into the cartridge body by laser etching, hot embossing or injection molding. The fluidic channels may be cuboid, cylindrical, or other feasible shape and dimension. Typically, the fluidic channels are approximately on the order of a few thousand square microns to ten thousand square microns. After the fluidic channels have been etched into the body of the cartridge, a top cover may be applied to the disposable sorter cartridge top surface to prevent evaporation and sample loss. The top cover may be coupled to the disposable sorter cartridge by adhesive means or by other binding methods.

Turning to FIGS. 4A-6, an exemplary embodiment of a disposable sorter cartridge 100 is shown. The cartridge 100 has an approximately rectangular thin and flat shape with a cartridge first end 102 and a cartridge second end 104. In general the dimensions of the disposable sorter cartridge 100 are between 5 cm and 10 cm (e.g., between 7-9 cm) in length, between approximately 1 cm and 4 cm in width (e.g., approximately 2.5 cm), and between about 2 and 6 mm (e.g., approximately 4 mm) in height. These dimensions may vary without necessarily affecting the functionality of the sorter cartridge, optimal disposable sorter cartridge 100 dimensions may be limited by the features of the flow cytometry apparatus used. In some variations, the cartridge 100 may have a symmetrically tapered cartridge second end 104. The symmetrically tapered end may allow the disposable sorter cartridge 100 to properly fit snugly within a flow cytometry system, while centering the droplet dispensing outlet 136.

In general, the cartridge 100 may include a sample compartment 110 (visible in the internal sectional view of FIG. 5). The sample compartment 110 may also include a sample loading aperture 112 which allows a user to load a microparticle sample using a conventional pipette. The sample compartment 110 may further include a vent 114. In some instances, when the disposable sorter cartridge 100 is within the corresponding flow cytometry apparatus, the sample loading aperture 112 and/or the vent 114 may be sealed and/or coupled (via gasket) to an air pressurizing system in the sorting device. In the examples shown in the figures, the sample compartment 110 tapers from its position near the cartridge first end 102 to the cartridge second end 104 such that a sample may be positioned for entry into the fluidic network and beginning the separation process of the microparticles within the sample.

The sample compartment 110 is in fluid communication with a main microfluidic channel 120. The microfluidic channel 120 in the examples shown run almost the entire length of the sorter cartridge 100 in a straight path. In general, the microfluidic channel 120 allows the sample to be drawn from the sample compartment down the length of the cartridge 100 towards the cartridge second end 104. The microfluidic channel 120 is configured to hold liquid. In some examples, the microfluidic channel 120 has a rectangular cross section having dimensions of approximately 50 μm-1000 um by approximately 5-200 μm. In other examples, the cross section of the microfluidic channel 120 may be other suitable shapes that possess similar cross sectional area. In some instances, a slight positive pressure (e.g. 1-2 psi) may be applied by the flow cytometry apparatus to either the sample loading aperture or the vent 114 to aid with sending the sample down the microfluidic channel 120.

Two flow adjust channels 122, also referred to herein as streamlining flow paths, are both in fluid connection with the microfluidic channel 120. As the figures show, both flow adjust channels 122 includes a flow adjust channel first end 124, 124' terminating in a port 126, 126'. This third 126 and fourth 126' ports may be connected (via a gasket or other seal) to a source of fluid in the sorting device. The fluid ports 126, 126' may therefore couple the two symmetric flow adjust channels 122, 122' with fluid reservoirs maintained within the flow cytometry apparatus for applying centering fluid into the sample from the sample compartment 110 traveling down the microfluidic channel of the cartridge for detection and sorting. The flow adjust channel converge on the main channel 120 at an intersection region 121. As can be seen in the figures, the two flow adjust channels 122, 122' are symmetrically arranged with respect to the microfluidic channel 120. In the present example, the two flow adjustment channels also have approximately the same cross sectional area as the microfluidic channel 120. In other examples, the two flow adjust channels 122 may possess different sized cross-sectional areas compared to the microfluidic channel 120. In use, fluid may be sent through the two flow adjust channels to center the sample along the microfluidic channel 120 as it flows down the microfluidic channel. While it may be possible to have fluid moving at different flow rates through the two flow adjust channels, more commonly, the two flow adjust channels will have the same flow rate. The flow rate of the two flow adjust channels may be adjusted to move microparticles through the microfluidic channel 120 one microparticle at a time in single file. Any of the cartridges described herein may not include a flow adjust channel (one or more flow adjust channels are not required for correctly sorting microparticles).

A detector region 150 (FIG. 8) will typically be located just past the intersection of the two flow adjust channels and the microfluidic channel 120. The detector region 150 may be configured to allow optical detection through the cartridge. Thus this region (and/or the entire cartridge) may be transparent to wavelengths used for detection. The detector region 150 may therefore be an optically transparent region that is aligned with the detector of the flow cytometry apparatus when the cartridge is engaged therewith. The detector region 150 may be configured to permit detection of microparticles passing this region along the microfluidic channel 120 to determine if they possesses a pre-determined characteristic (e.g. size, shape, optical property, and so forth). Information for each microparticle sensed by the detector of the flow cytometry apparatus, which may then, based on whether the microparticle possesses the pre-determined characteristic or not, provide control to briefly apply fluid flow into the second port 130 (inlet port) and therefore into the dispensing flow path to collect the identified microparticle by diverting it into the outlet flow path 134 as discussed below.

The sorting device may provide a delay between the time the detector interrogates the microparticle and applies fluid flow. The sorting device may be configured to operate on this delay based on the specific geometry of the cartridge.

As shown in FIGS. 4A and 5, a second fluid port 130 feeds into the dispensing flow path 131 that meets with the microfluidic channel at the sorting region 133 located distally beyond the intersection of the two flow adjust channels 122 and along the microfluidic channel 120. The second port 130 is configured for coupling to a corresponding flow cytometry apparatus and the sorting region also opens into the dispensing flow path 134 that is in fluid communication with the microfluidic channel 120. The dispensing flow path 134 terminates at the droplet dispensing port 136. In use, a fluid (e.g. buffer, biological media) may be applied through the second (inlet) port by the flow cytometry apparatus at a pre-calculated flow rate to move a microparticle into the dispensing flow path 134 and out of a droplet dispensing port 136 into a collection vessel if the microparticle has been determined to possess the pre-determined characteristic. If a microparticle has been determined to not possess the pre-determined characteristic, then flow rates through the second port 130 into the cartridge may be stopped by the sorting device allow the flow (including 'rejected' microparticles) to flow into the waste fluid path 915 which is an extension of the microfluidics channel 120 towards a first (waste) port 140. The portion of the waste fluid path in communication with the first port may have an enlarged diameter, as shown in greater detail in FIGS. 8, 9A and 9B. In some examples, the inlet flow path 131 has a cross-sectional area greater than that of the microfluidic channel 120. More specifically, the inlet flow path 130 has a cross-sectional area approximately 2×, 3×, 4×, 5×, 10×, 15×, 20×, 30×, 30×, 50×, etc. times greater than the cross-sectional area of the microfluidic channel 120. As can be seen from the figures, the sample collection channel (dispensing flow path 134) may bend and extends towards the distal end of the cartridge to connect to the droplet dispensing port 136.

The first port 140 may connect the waste outlet 144 of the waste flow path 915. The first (waste) port 140 may be coupled with the flow cytometry apparatus. The flow cytometry apparatus may apply pressure (e.g., negative pressure) through the first port 140 either constantly. In general, the first port 140 may have a cross-sectional diameter equal or greater than that of the second port 130.

FIGS. 7A and 7B resemble the variations shown in FIGS. 4A-6, but include exemplary dimensions.

FIG. 8 shows the relationship between the streamlining fluid paths 805, 805' and the microfluidic channel. In particular, the third and fourth ports 801, 801' are shown positioned on the upper (top) surface at an angle α that is between about 20 degrees and 60 degrees relative to the long axis 801 through the midline of the elongate body of the cartridge. The third port (fluid streamlining port) and the fourth port (fluid streamlining port) may be spaced a distance 811 of between about 14-16 mm from the first (waste) port 140. The streamlining fluid paths may be connected to the third and fourth ports and may symmetrically intersect the microfluidics channel 120 at an intersection region 844.

In FIGS. 9A and 9B, sectional and sectional perspective views (respectively) of the distal end of the cartridge illustrate the spatial relationship between the waste (first) port 140 and the dispensing (second) port 130. In this example, the first port has a diameter 903 that is larger than the diameter of the second port 911 (e.g., 1.5×, 2×, 3×, 4×, 5×). The two ports are separated by a distance 905 along the midline longitudinal axis 801 that is typically between 1-3 mm. The detection region 150 is between the second port and the intersection region of the streamlining fluid paths 805 with the microfluidics channel 120, along the microfluidics channel. In this example, the droplet dispensing outlet includes a cannula 869 extending from the distal end of the cartridge.

Group Sorting and Isolation of Individual Microparticles

Figures 13A, 13B:
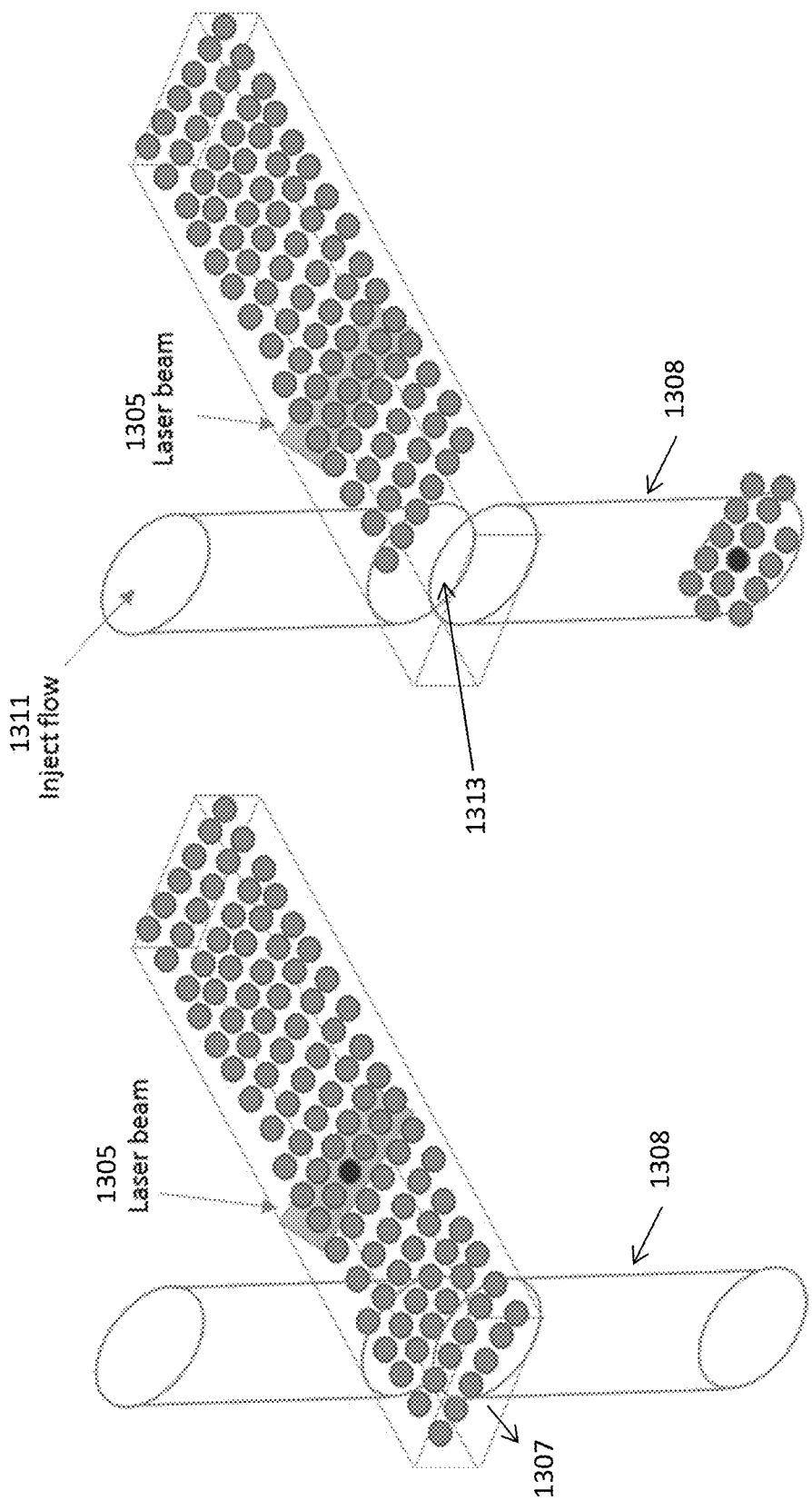
FIGS. 13A and 13B illustrate one method of sorting and dispensing cells using a bulk sorting method as described herein; in this example, groups of cells are sorted using a fluid switch by injecting flow.

As mentioned above, any of the methods and apparatuses described herein may be used for sorting or sorting and dispensing individual microparticles, such as a single cell or groups of cells. There is a need for simple devices that can sort microparticles (e.g., cells) at high rate, ideally more than 100,000 microparticles per second and yet can still isolate very rare microparticles, such as circulating tumor cells in cancer patient's blood or fetal cells in pregnant woman's blood. In these cases, the frequency of rare cells may be one in a million to one in a billion. Directly isolating these extremely rare cells cannot be achieved using current cell sorting devices which typically have sorting rates that are too slow. Currently available sorting methods require cells 1103 to move in the sorting region of the device in a single file line, one by one (see, e.g., FIG. 11), in a direction of flow 1107 through the microfluidics channel for illumination and detection 1105. These apparatuses and methods typically require that there is enough distance between each cell in the single file arrangement so that each individual cell would be interrogated by laser and be sorted, one-by-one. This "one-by-one" sorting greatly limits how fast cells can be sorted. Some variations of the methods of cell sorting described herein may instead move cells in bulk in the microfluidic channel. Cells may pass the focused laser beam(s) continuously in groups of hundreds or thousands, instead of one by one, which dramatically increases sorting speed. See, e.g. FIG. 12, which shows a schematic of large groups of cells 1202 passing through a sensing region including a laser illumination source 1205 that may allow simultaneous interrogation of the group of cells by one or more detectors, to determine if one or more of the cells in the group has predetermined characteristic. By sorting cells in bulk, it dramatically increases number of cells can be sorted. This method is particularly useful for isolating extremely rare cell, such as circulating tumor cells or circulating fetal cells. In FIG. 12, the majority of the cells (grey) are unwanted cells which do not have a fluorescence signal when illuminated. An example of a target cell 1209 is shown colored black. When the target cell passes though the interrogation region (laser 1205), it may generates a strong fluorescence signal. Using the flow sorting method and apparatus described herein, the target cell 1209 may be captured in a single droplet (e.g., about 1 μl droplet). FIGS. 13A and 13B illustrates detection and capture of a target cell. Briefly, in FIG. 13A, the bulk of cells are moving through microfluidic channel in a direction of flow 1307. When the target cell(s) passes through the detection region (laser beam 1305), it generates a fluorescent signal. The unwanted cells (grey cells) that do not generate fluorescent signal (or not a sufficiently high-intensity signal) continue to pass in the direction of flow 1307. However, when the fluorescence signal is detected from the group of cells in the detection region 1305, the sorting device will divert the group of cells into open a sample outlet flow path 1308 for separation (and/or dispensing). As discussed below, any appropriate valve may be used (including acoustic, electrical/magnetic, etc.) but in FIGS. 13A and 13B, the example shows a flow valve. As shown in FIG. 13B, in this example, the flow valve briefly, in some variations after small amount of delay, opens an injection flow 1311. A delay may be included and calculated so that valve opens only when the target cell enters the injection flow area 1313. The injected flow 1311 may dispense the target cell out of a nozzle, along with the adjacent cells in the group. Cell sorting is achieved, although complete sorting has not been achieved. Additional isolation steps may then be taken either immediately (e.g., in another part of the cartridge or recycling through the same detection region) or serially, e.g., using a different cartridge. Even though some unwanted cells (the grey cells) will come with the target cell (the black cell), huge numbers of cells can be sorted during short period of time. FIGS. 13A and 13B only show one layer of cells passing through microfluidic channel. In practice, multiple layers of cells can pass through the microfluidic channel at the same time, which may further increase sorting rate. For example, the dimension of microfluidic channel may be >4× the diameter of the target microparticle wide by >2× the diameter of the target microparticle deep (e.g., about 100 μm by 20 μm, 120 μm by 30 μm, 150 μm by 50 μm, 200 μm by 60 μm, etc.). The diameter of the injection flow path may be, for example, 150 μm. Undiluted blood typically contains $3\times10^6$ red blood cells per microliter. When an undiluted blood sample passes through the microfluidic channel at the rate of 0.5 μL/s, the overall sorting rate may be $3\times10^6 \times 0.5 = 1.5\times10^6$ per second. It is more than 10-fold faster than current sorting methods. For a microfluidic channels with cross-sections of approximately 150 μm×50 μm and a length of 20 mm, to reach flow rate of 0.5 ul/s, only about 1 psi pressure is needed. If the diameter of injection flow is the same as the width of the channel (e.g., 150 μm), there are total about 3000 unwanted cells will be captured with wanted cell. Even though this bulk sorting method does not produce a pure cell population, it provides a very fast way to enrich very rare cells. Pure cell isolation can be achieved by sorting the resulting bulk sorted sample again using one-by-one sorting.

The bulk sorting described here is well suited for isolating extreme rare cells from a large number of unwanted cells. The rarer the target cells are, the more fold of enrichment may be achieved. For example, if there is only one target cell in 1 ml of blood which contains $3\times10^9$ red blood cells, using current sorting methods (with a maximum sorting rate 100,000 per second), it would take 8 hours to sort through all of these cells. Using the bulking sorting described herein at 0.5 μL/s, it would only take approximately 33 minutes to enrich from 1 in $3\times10^9$ to 1 in 3000. This is 1 million-fold enrichment in 33 minutes. Isolation of the single target cell using a follow-on one-by-one sorting (e.g., as described herein, by passing the selected group(s) of cells through the detection microfluid channel using streamlining fluid, and/or simply diluting the fluid sufficiently) can be done in 2 minutes at sorting rate of 20 cells per second, because there are only 3000 unwanted cells for each wanted cell during bulk soring. The fold of enrichment can drop quite quickly if the number of target cells in the initial sample (e.g., 1 ml of blood) is high. For example, if there are N targeted cells in 1 ml of blood ($3\times10^9$ cells), fold of enrichment=$1\times10^6/N^2$. In the case of either circulating cancer cells or circulating fetal cells, typically there are only a few cells in 1 ml of blood. Therefore, bulk sorting is capable to sort 1 billion cells in 10 minutes and reach 1 million-fold enrichment. Thus any of the bulk sorting methods described herein are particularly well suited to instance in which the concentration of target cells (N) is quite rare (e.g., where the size of the group of simultaneously sorted cells is sufficiently sized so that is unusual for each group to include even one target cell. If the probability of each group including a target cell is high, then the bulk sorting method described herein may not be beneficial. For example, when dividing the sample into arbitrary groupings of x microparticles, if the probability of each group of x microparticles having a target cell is approximately z percent, it may be beneficial to apply the bulk sorting technique described herein where z percent is less than 50% (e.g., less than 40%, less than 30%, less than 20%, less than 15%, less than 10%, less than 9%, less than 8%, less than 7%, less than 6%, less than 5%, less than 4%, less than 3%, less than 2%, less than 1%, less than 0.5%, etc.). Typically, the scarcer the target cell, the greater the fold-increase in enrichment.

A bulk sorting rate can be increased further by simply increasing the pressure applied to the microfluidic channel and/or by reducing the length of the microfluidic channel. If the length of the microfluidics channel (including the detection/sensing region) is decreased from 20 mm to 10 mm, the flow rate may increase to 1 μL per second. Therefore, the sorting rate will increase to 3 million cells per second. Alternatively, without changing the dimension of the microfluidic channel, increasing pressure from 1 psi to 2 psi will also increase sorting rate to 3 million cells per second.

The number of unwanted cell brought along with target cell(s) may be proportional to the cross-section area of injection flow. The smaller the cross-section area of injection flow, the fewer unwanted cells will be in the group and therefore will be brought along the target cell(s), and the higher fold of enrichment will be.

Figure 14:
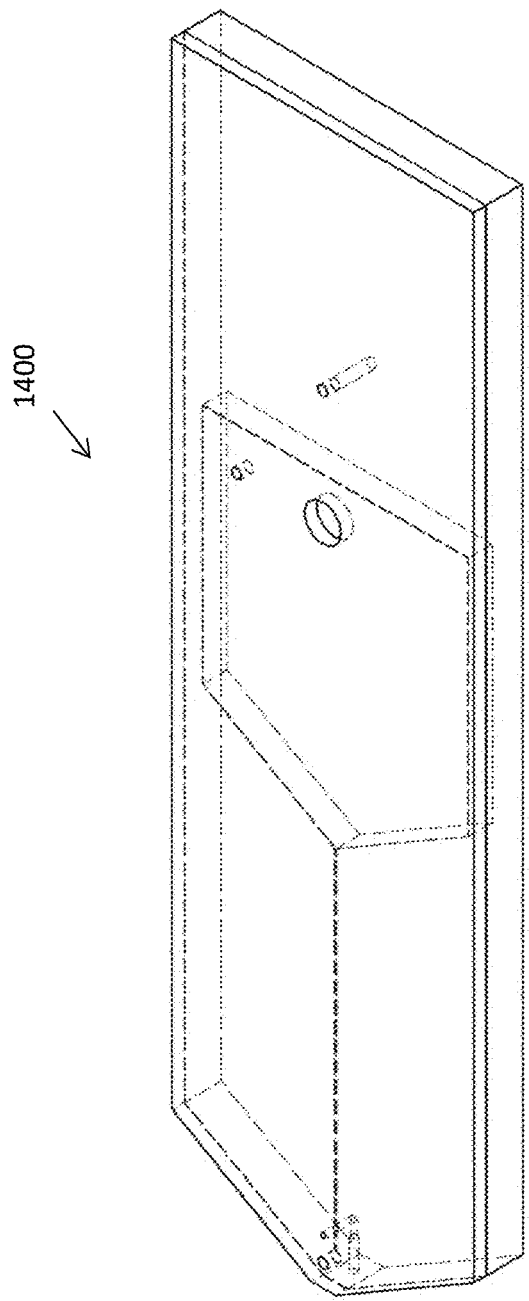
FIG. 14 schematically illustrates one example of a cartridge 1400 for performing bulk sorting, as described herein.

FIG. 14 illustrates an example of a microfluidic cartridge configured for bulk sorting using a fluid valve, as described herein. This example is similar to the removable microparticle sorter cartridge shown in FIGS. 4A-9B, described above. By comparison, the principle difference is that the bulk sorting microfluidic cartridge shown in FIG. 14 does not include sheath flow paths (compare to streamlining fluid paths 805, 805' shown in FIG. 8) which may be used for sorting cells in a single file manner. Alternatively the same cartridges shown in FIGS. 4A-9 may be used, but without applying any fluid from the streamlining fluid path(s).

Figure 15:
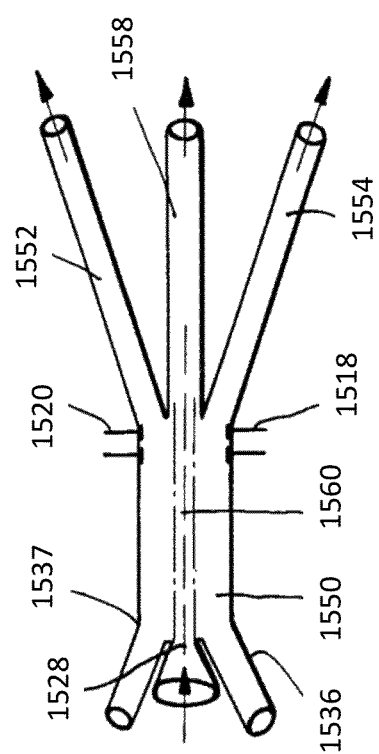
FIG. 15 is an example adapted from U.S. Pat. No. 4,175,662 showing sorting using gas impulse.

As mentioned, the bulk sorting techniques described herein may be applied to any appropriate type of microfluidic sorting technique. For example, U.S. Pat. No. 4,175,662 to Zold, illustrated in FIG. 15 (adapted from Zold), describes a gas impulse sorting technique used in a single-file method, which deflects a target cell by producing a gas impulse from a pair of electrodes 1520 and 1518 to deflect a particle stream which was hydrodynamically focused into the center of the channel 1560. Because particles are moving along the center of the channel one by one, individual particles may be deflected for sorting at a sorting rate of 400-500 beads per second. This technique may be modified, for example, by configuring the device to sort groups of particles moving along the center of the channel in bulk. By this technique, sorting rate can increase hundreds and thousands fold. U.S. Pat. No. 7,392,908 to Frazier also describes a hydrodynamic focusing sheath fluid to move particles along the center of the sorting chamber one by one so that each particle could be sorted by an impulse generator. Rather than directing the stream of particles in a single-file line for sorting as descried in Frazier, passing a bulk group of particles and displacing the entire bulk of particles when a target is detected as described herein, even when displacing by an impulse generator, may improve the sorting rate by hundreds and thousands fold.

Figure 16:
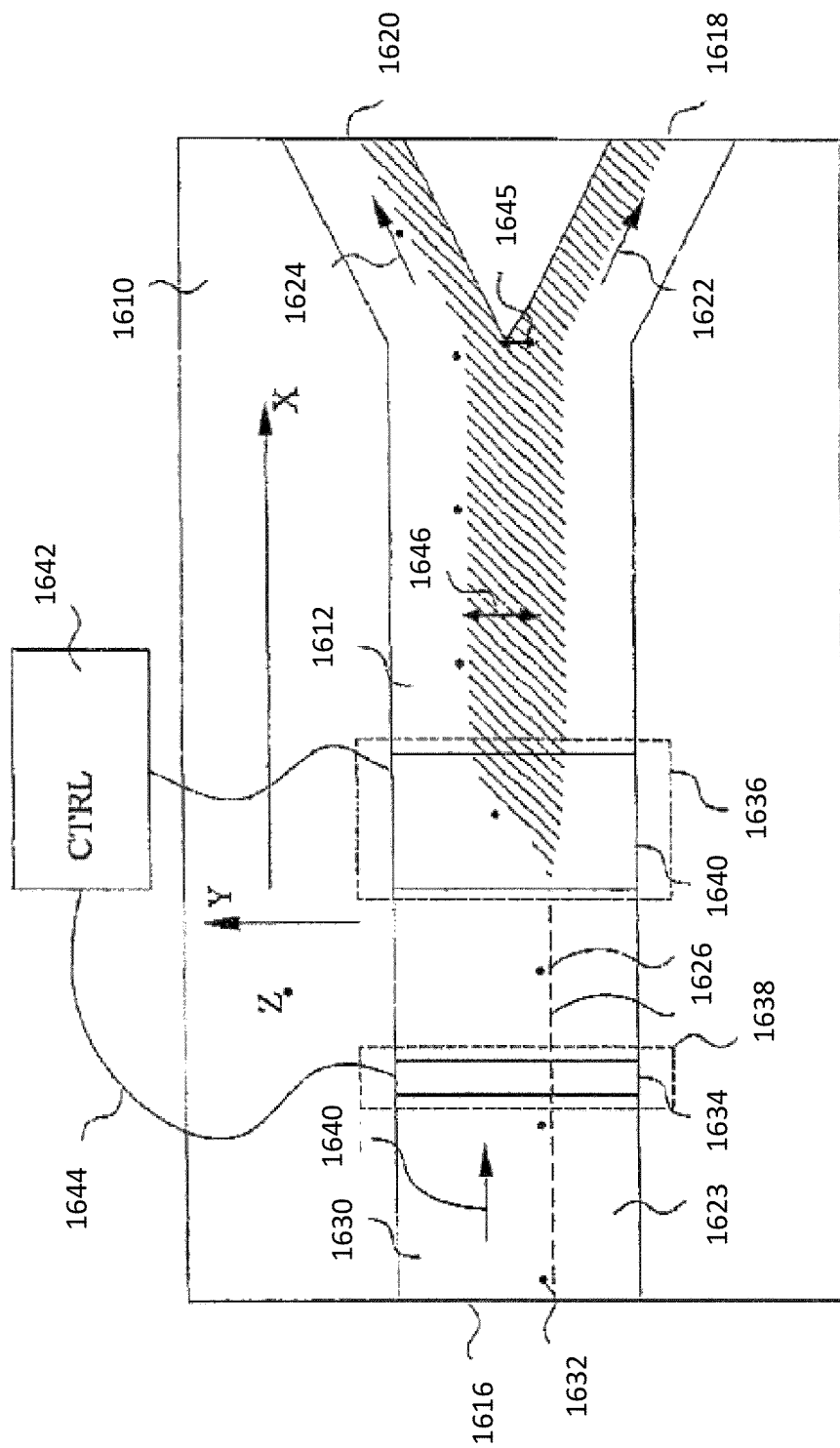
FIG. 16 is an example adapted from U.S. Pat. No. 8,387,803 showing an acoustic method that may be used for bulk sorting as described herein.

Similarly, U.S. Pat. No. 8,387,803 to Thorslund describes the use of an acoustic standing wave to move particles between two channels, again describing the use of single-file particles. FIG. 16 (adapted from Thorslund) one configuration of such a device, using single-file sorting. The lateral movement of the particles was achieved by applying an acoustic standing wave generated by 1636. If particles move in bulk, the sorting rate can increase hundreds and thousands fold.

In any kind of microfluidic sorting device, the throughput of bulk sorting may depend on how fast bulk particles are moving through the microfluidic channel and how large the displacement volume during the sorting is. The higher the speed at which the bulk particles move in the channel, the higher sorting rates may be. The larger the displacement volume is, the higher sorting rate may be. The larger displacement volume may increase the sorting rate because more particles can be packed into the displacement volume. In any of the variations described herein, the illumination/detection size (e.g., the laser beam spot) may have an elongated shape so that it covers the whole channel area where the groups of particles move. Also, the laser intensity may be distributed evenly across the whole elongated detection (e.g., laser beam spot) region. This may be achieved by generating a top-hat laser beam shape, for example. Uniform laser intensity can also be generated by internal refraction induced by microfluidic channel walls.

Methods of Using the Cartridge

The methods described herein are for sorting microparticles contained within a bulk fluid sample may be based on a pre-determined characteristic of the microparticles using any of the cartridges described herein in conjunction with a sorting device (e.g., the flow cytometry devices described herein). The pre-determined characteristic may be size, shape, unique morphology, fluorescent intensity, optical quality either innate or introduced subsequently within the lab, and so forth. The elegance and simplicity of the microparticle sorting methods using the cartridges 100 described herein is based on the specific arrangement of the channels and inlets along the length of the disposable sorter cartridge 100.

The cartridge 100 may be used to sort microparticles contained within a fluidic medium. The microparticles may be cells, agglomeration of cells, or other particulates, either organic or inorganic. Typically the microparticles are less than 500 μm, less than 50 μm, less than 5 μm, and so forth.

Figure 10:
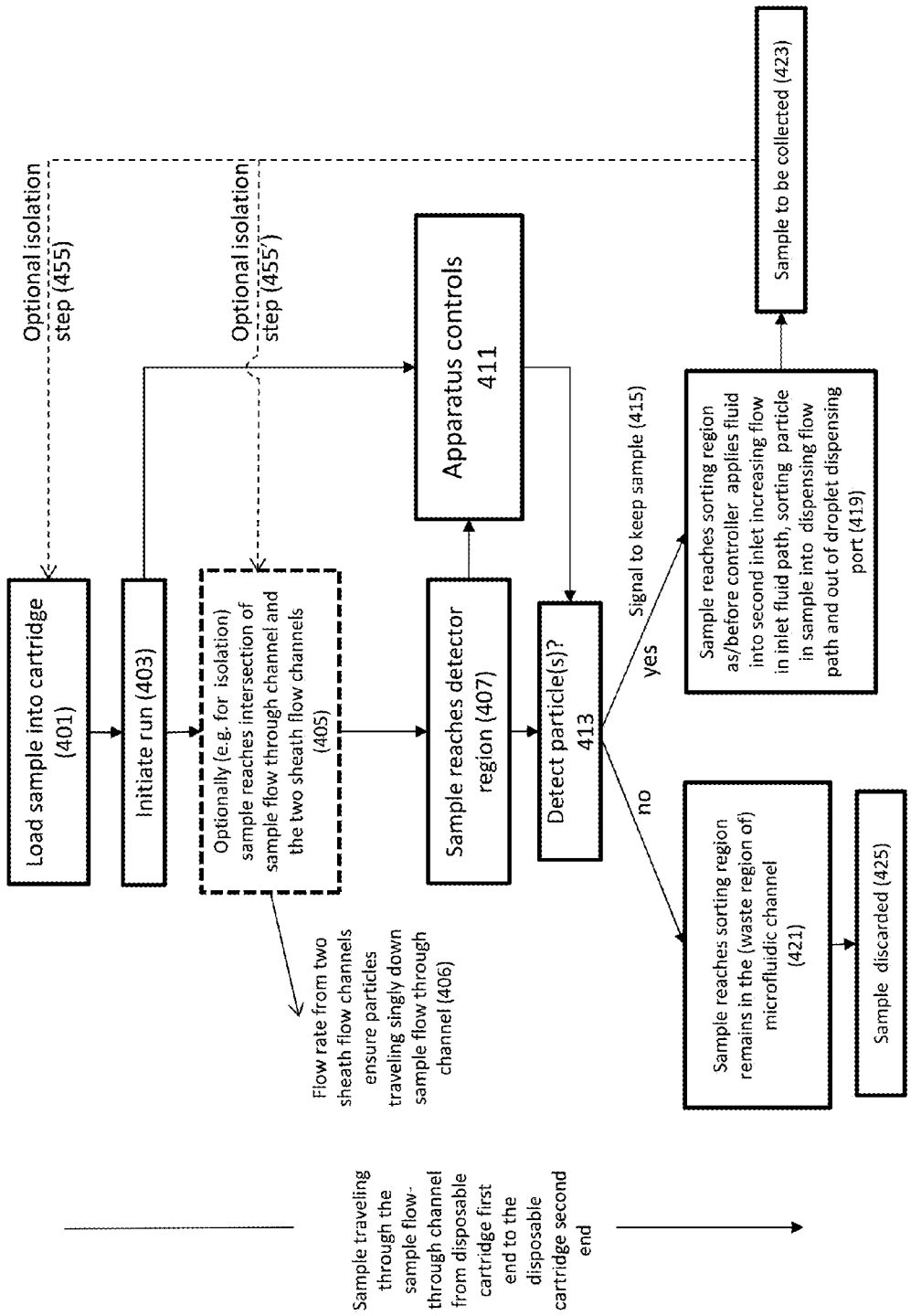
FIG. 10 is a flow chart depicting how microparticles are sorted and retained or discarded using a cartridge as described herein.

In general, the methods of sorting microparticles include adjusting the amount of force exerted on the fluidic sample as well as the directionality of the forces through adjusting the fluid flow rate through the fluidic channels. A summary flowchart of the operation of a cartridge for sorting and subsequent capture and retention of those microparticles having the pre-determined characteristic is shown in FIG. 10. In general, a sample is first introduced into the sample compartment 110 of the disposable sorter cartridge 100 through the sample loading aperture 112 at step 401. The sample compartment 110 may hold approximately microliters, tens of microliters, or hundreds of microliters of sample. Once a sample has been loaded into the sample compartment 110 and a run initiated (step 403), an initial negative pressure may be applied to the main channel 120 through first inlet 140. The sample may then travel down the microfluidic channel 120, added by capillary action. In some instances, it may also be feasible to apply a small amount of positive pressure at the sample loading aperture 112 and/or vent to aid with sending the sample through the beginning portions of the microfluidic channel 120.

Optionally, the method may include selecting between bulk sorting (e.g., sorting groups of microparticles or individual microparticles. For example, in some variations the microparticles may be arranged in a single-file arrangement within the microfluidic channel including the detector 405. As the fluidic sample travels down the microfluidic channel 120 from the cartridge first end 102 to the cartridge second end 104, fluid such as buffer, solvent, or biological media (depending upon the microparticle sample being interrogated) may be introduced through the two flow adjust channels 122 to center the fluidic sample down the microfluidic channels 120 (step 405). While not shown, reservoirs retained with the flow cytometry apparatus may be pressurized to attain flow rates that result in the targeted sample moving through the microfluidic channel 120 at a desired rate as well as having each microparticle moving singly down the microfluidic channel 120. The fluid flow rate through the various channels of the fluidic network may be based upon the initial flow rate of the fluid, the distance from the initial point where the fluid flow rate is known and the cross-sectional diameter of the channel in which the fluid is flowing. Similarly, the amount of pressure may also be calculated.

As can be seen from the figures, the two flow adjust channels 122 that terminate at a single location along the main channel 120 are identical in their spatial arrangement to the main channel 120. In other examples, the two flow adjust channels 122 may be asymmetric relative to the main channel 120, have different lengths, and/or have different cross-sectional areas. In this current example, the two flow adjust channels 122 form equal acute angles with the easily channel 120. In this current configuration, the two flow adjust channels 122 form approximately a 45° angle with the main channel 120. This configuration is preferred because angles less than 45° or greater than 45° may not be able to adequately center the microparticles in channel 120. Also because the two flow adjust channels 122 are identical in positioning as well as dimensions, a single control may be used for controlling the flow rate through these channels further simplifying the overall apparatus controls and/or programs. In use, the two flow adjust channels 122 provide equal fluid flow to the main channel 120 such that a single microparticle at a time travels down the main channel 120. Alternatively, the microparticles may be passed down through the microfluidics channel in groups (see, e.g., FIGS. 12 and 13A-13B).

As mentioned earlier, the detection region 150 is located between the intersection point of the two flow adjust channels 122 with the microfluidic channel 120 and the sorting region. The sorting of the microparticles is directed in the detection region 150 (step 407) using the apparatus. The flow cytometry apparatus receives signal from detection region 150 to interrogate the microparticles in the fluidic stream as they pass the detection region 150 along the microfluidic channel 120 (step 413). The detector may continuously monitor the stream of sample fluid or may monitor only at discrete periods based on the flow rate of the fluidic sample. If the detector establishes that a microparticle queried possesses the pre-determined characteristic, the apparatus may capture the microparticle (step 413) by activating flow through the second port and down the dispensing flow path. The system may include a delay time between when the detector determines whether a microparticle is to be sent to the sample receptacle when the flow cytometry apparatus controller opens fluid through the second port for dispensing the microparticle out of droplet dispensing port.

The first (waste) port further functions to draw microparticles not possessing the pre-determined characteristic toward it. The waste path is in-line (though it may not be) with the microfluidic channel and connects to the waste port. In the instance where the microparticle is intended to travel to the waste, the microparticle will pass the sorting region into the waste fluid path and out of the waste port. In order to prevent microparticles not possessing the pre-determined characteristic from entering the dispensing flow path, a slight amount of negative pressure may be applied at the first port. A small amount of negative pressure (e.g. between 0.2 psi and 4 psi) may be applied continuously or intermittently to bring the waste solution to the waste port (step 425).

Groups of particles or single particles that have the desired characteristic (e.g., florescence) may be directed to the sample outlet flow path 419, for collection 423 or further processing (e.g., isolation of single cells or smaller groups of cells 455, 455'). For example, collected samples may be re-loaded into the same cartridge or a different (new) cartridge 455, for further isolation, e.g. by running them through the microfluidics channel in a single-file manner 405. In some variations, the sample may be directly connected to a second microfluidics channel 455' for running in single-file line and isolating in dispensing droplets 419.

As described above, the disposable sorter cartridge has many advantages over currently available cartridges used for flow cytometry. Because of the simplicity of the disposable sorter cartridge makes it relatively inexpensive to manufacture. By coordinating the application of only small amounts of positive and negative pressure at various points along the fluidic pathway, a mixture of microparticles may be precisely sorted based on a certain characteristic. Thus, it would be cost effective to replace the cartridge every time a new sample has to be run.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of bulk sorting microparticles, the method comprising:
   passing a group of microparticles surrounded by fluid into a detection region of a first switch, wherein a plurality of microparticles within the group of microparticles are adjacently arranged within the detection region perpendicular to a direction of flow of the group of microparticles through the detection region;
   simultaneously examining the plurality of microparticles within the detection region to detect when at least one microparticle in the group of microparticles has a predetermined characteristic;
   passing the group of microparticles into a sample outlet flow path when at least one microparticle in the group of microparticles has the predetermined characteristic, otherwise passing the group of microparticles through the first switch into a waste outlet flow path; and
   isolating the at least one microparticle having the predetermined characteristic from the group of microparticles by passing the group of microparticles dispensed from the sample outlet through a second switch in a single-file arrangement through a detection region of the second switch, passing the at least one microparticle having the predetermined characteristic into a second sample outlet flow path of the second switch when the at least one microparticle is detected within a detection region of the second switch, and passing microparticles from the group of microparticles that do not have the predetermined characteristic into a waste outlet flow path of the second switch.

2. The method of claim 1, wherein the switch is a flow switch.

3. The method of claim 1, wherein simultaneously examining comprises changing a flow rate of the fluid surrounding the group of microparticles from a first flow rate to a second flow rate when at least one microparticle in the group of microparticles has the predetermined characteristic and is present in the switch.

4. The method of claim 3, wherein changing the flow rate of the fluid surrounding the group of microparticles comprises adding or subtracting fluid surrounding the group of microparticles.

5. The method of claim 1, wherein simultaneously examining comprises changing a flow rate of the fluid surrounding the group of microparticles from a first flow rate to a second flow rate when at least one microparticle in the group of microparticles has the predetermined characteristic and is present in the switch, and wherein passing the group of microparticles into the sample outlet flow path comprises passing the group of microparticles into the sample outlet flow path and dispensing the group of microparticles out of the sample outlet flow path when the fluid surrounding the group of microparticles is traveling through the switch at approximately the second flow rate, otherwise passing the group of microparticles through the switch into the waste outlet flow path when the fluid surrounding the group of microparticles is traveling through the switch at approximately the first flow rate.

6. The method of claim 1, wherein isolating the at least one microparticle comprises passing the group of microparticles dispensed from the sample outlet through the second switch in which the second switch comprises the first switch.

7. The method of claim 1, wherein passing the group of microparticles into the detection region comprises passing the group of microparticles through a cartridge containing the switch.

8. The method of claim 1, wherein the resistance to fluid flow along the waste outlet flow path is higher than the resistance to fluid flow along the sample outlet flow path.

9. The method of claim 1, wherein the group of microparticles is a group of cells.

10. The method of claim 1, wherein the detected predetermined characteristic is selected from one or more of: shape, size, and fluorescence intensity.

11. The method of claim 1, further comprising pressurizing the fluid surrounding the group of microparticles to a predetermined pressure or range of pressures.

12. The method of claim 1, further comprising dispensing the at least one microparticle having the predetermined characteristic from the sample outlet of the second switch.

* * * * *